(12) United States Patent
Tendler et al.

(10) Patent No.: US 11,629,176 B2
(45) Date of Patent: Apr. 18, 2023

(54) NATIVE CELL DERIVED VESICLES CONTAINING TUMOR SUPPRESSOR PROTEINS FOR THERAPY

(71) Applicant: Exoprother Medical Ltd., Haifa (IL)

(72) Inventors: Alexander Tendler, Haifa (IL); Lana Volokh, Haifa (IL)

(73) Assignee: Exoprother Medical Ltd., Haifa (IL)

( * ) Notice: Subject to any disclaimer, the term of this patent is extended or adjusted under 35 U.S.C. 154(b) by 881 days.

(21) Appl. No.: 16/495,425

(22) PCT Filed: Mar. 21, 2018

(86) PCT No.: PCT/IL2018/050328
§ 371 (c)(1),
(2) Date: Sep. 19, 2019

(87) PCT Pub. No.: WO2018/173059
PCT Pub. Date: Sep. 27, 2018

(65) Prior Publication Data
US 2020/0071373 A1 Mar. 5, 2020

Related U.S. Application Data

(60) Provisional application No. 62/474,142, filed on Mar. 21, 2017.

(51) Int. Cl.
| | | |
|---|---|---|
| C07K 14/47 | (2006.01) | |
| A61K 47/69 | (2017.01) | |
| A61P 35/00 | (2006.01) | |
| A61K 35/30 | (2015.01) | |
| A61K 38/00 | (2006.01) | |

(52) U.S. Cl.
CPC .......... *C07K 14/4746* (2013.01); *A61K 35/30* (2013.01); *A61K 47/6901* (2017.08); *A61P 35/00* (2018.01); *A61K 38/00* (2013.01)

(58) Field of Classification Search
CPC ................................................ C07K 14/4746
See application file for complete search history.

(56) References Cited

U.S. PATENT DOCUMENTS

| | | | |
|---|---|---|---|
| 2010/0092524 A1 | 4/2010 | Taylor et al. | |
| 2012/0093885 A1 | 4/2012 | Sahoo et al. | |
| 2013/0243820 A1 | 9/2013 | Taylor et al. | |
| 2015/0079631 A1* | 3/2015 | Breakefield | A61K 31/7105 |
| | | | 435/69.1 |
| 2016/0331686 A1 | 11/2016 | Polach et al. | |

FOREIGN PATENT DOCUMENTS

| | | |
|---|---|---|
| CN | 103237901 | 8/2013 |
| WO | WO 2013/048734 | 4/2013 |
| WO | WO 2013/138427 | 9/2013 |
| WO | WO 2014/168548 | 10/2014 |
| WO | WO 2015/085096 | 6/2015 |
| WO | WO 2018/173059 | 9/2018 |
| WO | WO 2018/173059 A9 | 9/2018 |

OTHER PUBLICATIONS

Tendler et al. (Features of p53 protein distribution in the corneal epithelium and corneal tear film. Sci Rep 10, 10051 (2020). https://doi.org/10.1038/s41598-020-67206-z) (Year: 2020).*
Han, Kyu-Yeon, et al. "Potential role of corneal epithelial cell-derived exosomes in corneal wound healing and neovascularization." Scientific reports 7.1 (2017): 1-14 (published Feb. 6, 2017) (Year: 2017).*
Notification of Office Action dated Feb. 22, 2022 From the State Intellectual Property Office of the People's Republic of China Re. Application No. 201880033490.1.(8 Pages).
Translation Dated Mar. 15, 2022 of Notification of Office Action dated Feb. 22, 2022 From the State Intellectual Property Office of the People's Republic of China Re. Application No. 201880033490. 1. (9 Pages).
Supplementary European Search Report and the European Search Opinion dated Sep. 22, 2020 From the European Patent Office Re. Application No. 18772626.0. (11 Pages).
Notification of Office Action and Search Report dated Aug. 25, 2022 From the State Intellectual Property Office of the People's Republic of China Re. Application No. 201880033490.1 and Its Translation of Office Action Into English together with an English Summary. (10 Pages).
Vinyals et al. "Failure of wild-type p53 gene therapy in human cancer cells expressing a mutant p53 protein", Gene Therapy 6:22-33, Jan. 15, 1999.
International Preliminary Report on Patentability dated Oct. 3, 2019 From the International Bureau of WIPO Re. Application No. PCT/IL2018/050328. (8 Pages).
International Search Report and the Written Opinion dated May 30, 2018 From the International Searching Authority Re. Application No. PCT/IL2018/050328. (12 Pages).
Burdakov et al. "Exosomes Transfer P53 Between Cells and Can Suppress Growth and Proliferation of P53-Negative Cells", Cell and Tissue Biology, 12(1): Jan. 20-26, 2018.
Gabrilovich "INGN 201 (Advexin®): Adenoviral P53 Gene Therapy for Cancer", Expert Opinion on Biological Therapy, 6(8): 823-832, Published Online Jul. 20, 2006.

(Continued)

*Primary Examiner* — Scott Long

(57) ABSTRACT

A method of obtaining cell derived vesicles comprising an active wild-type p53 is disclosed. The method comprising: (i) isolating cell derived vesicles from a biological sample comprising cells; and (ii) treating the cell derived vesicles with a DNA damaging agent, or the method comprising: (i) treating cells with a DNA damaging agent; and (ii) isolating cell derived vesicles from a biological sample comprising the cells. A proteinaceous preparation comprising cell derived vesicles and a pharmaceutical composition comprising the proteinaceous preparation are also disclosed. Methods of treating a disease, disorder or condition associated with a mutant or a nonfunctional p53 protein and methods of inducing apoptosis of a target cell comprising a mutant or a nonfunctional p53 protein are also disclosed.

12 Claims, 21 Drawing Sheets
(13 of 21 Drawing Sheet(s) Filed in Color)

(56) References Cited

OTHER PUBLICATIONS

Heath "An Investigation Into the Role of Microvesicles in Mutant P53 Invasive Gain-of-Function", PhD Thesis, University of Glasgow, UK, 3 P., 2015. Abstract.

Kim et al. "Development of Exosome-Encapsulated Paclitaxel to Overcome MDR in Cancer Cells", Nanomedicine: Nanotechnology, Biology, and Medicine, 12(3): 655-664, Published Online Nov. 14, 2015.

Lane et al. "P53-Based Cancer Therapy", Cold Spring Harbor Perspectives in Biology, 2(9): a001222-1-a001222-24, Sep. 2010.

Pokroy et al. "P53 Expression in the Normal Murine Eye", Investigative Ophthalmology & Visual Science, 43(6): 1736-1741, Jun. 2002.

Tendler et al. "Identification of Cytoplasmic P53 Protein in Corneal Epithelium of Vertebrates", Experimental Eye Research, 82(4): 674-681, Available Online Dec. 22, 2005.

Tendler et al. "P53 Protein Subcellular Localization and Apoptosis in Rodent Corneal Epithelium Cell Culture Following Ultraviolet Irradiation", International Journal of Molecular Medicine, 31(3): 540-546, Mar. 2013.

Tendler et al. "Possible Reason for Accumulation of P53 in the Cytoplasm of Corneal Epithelium", International Journal of Molecular Medicine, 31(3): 540-546, Pubhshed Online Jan. 16, 2013. Abstract.

Tendler et al. "Tissue-Specific P53 Expression in the Nervous System", Molecular Brain Research, 72(1): 40-46, Sep. 8, 1999.

Tickner et al. "Functions and Therapeutic Roles of Exosomes in Cancer", Frontiers in Oncology, 4(Art. 127): 1-8, May 27, 2014.

Trivedi et al. "Modification of Tumor Cell Exosome Content by Transfection With Wt-P53 and MicroRNA-125b Expressing Plasmid DNA and Its Effect on Macrophage Polarization", Oncogenesis, 5(7): e250-1-e250-12, Published Online Aug. 8, 2016.

Yim et al. "Exosome Engineering for Efficient Intracellular Delivery of Soluble Proteins Using Optically Reversible Protein-Protein Interaction Module", Nature Communications, 7: 12277-1-12277-9, Published Online Jul. 22, 2016.

Yu et al. "The Regulation of Exosome Secretion: A Novel Function of the P53 Protein", Cancer Research, 66(9): 4795-4802, May 1, 2006.

Office Action dated Oct. 19, 2022 From the Israel Patent Office Re. Application No. 269483. (4 Pages).

Notification of Office Action and Search Report dated Jun. 3, 2021 From the China Intellectual Property Administration Re. Application No. 201880033490.1 and Its Translation of Office Action Into English. (23 Pages).

\* cited by examiner

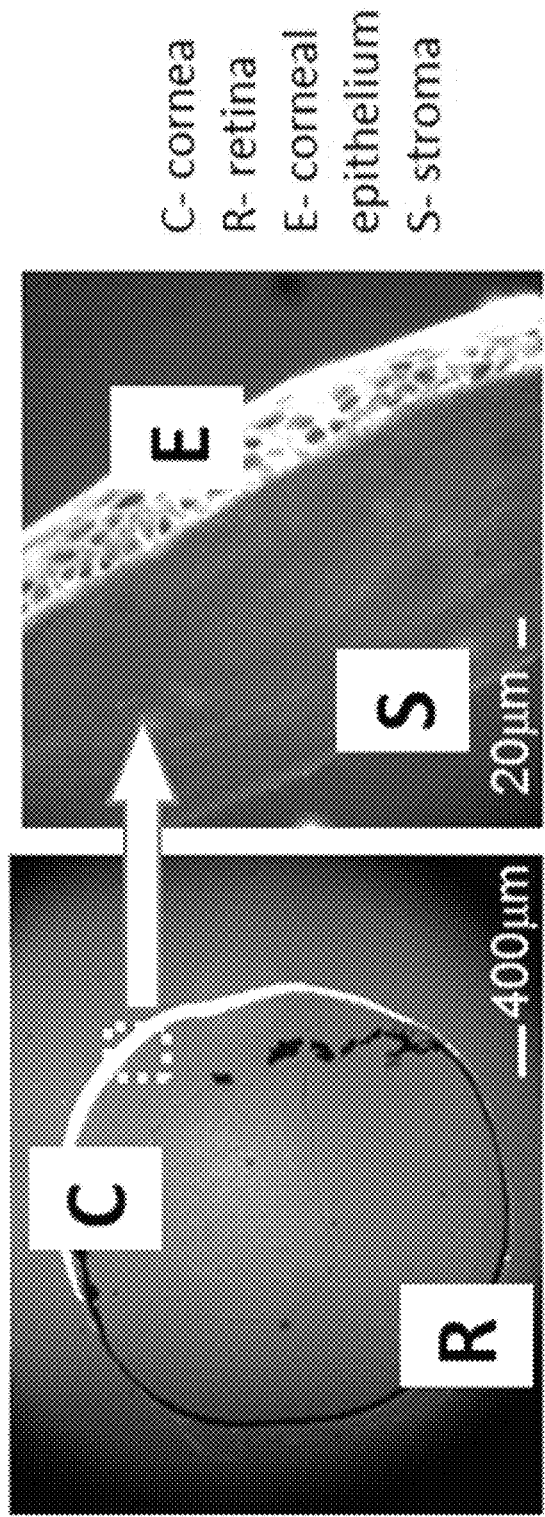

Incorporated from Tendler Y et al., *International Journal of Molecular Medicine* (2015) 36, Suppl. 1, Abstract 463

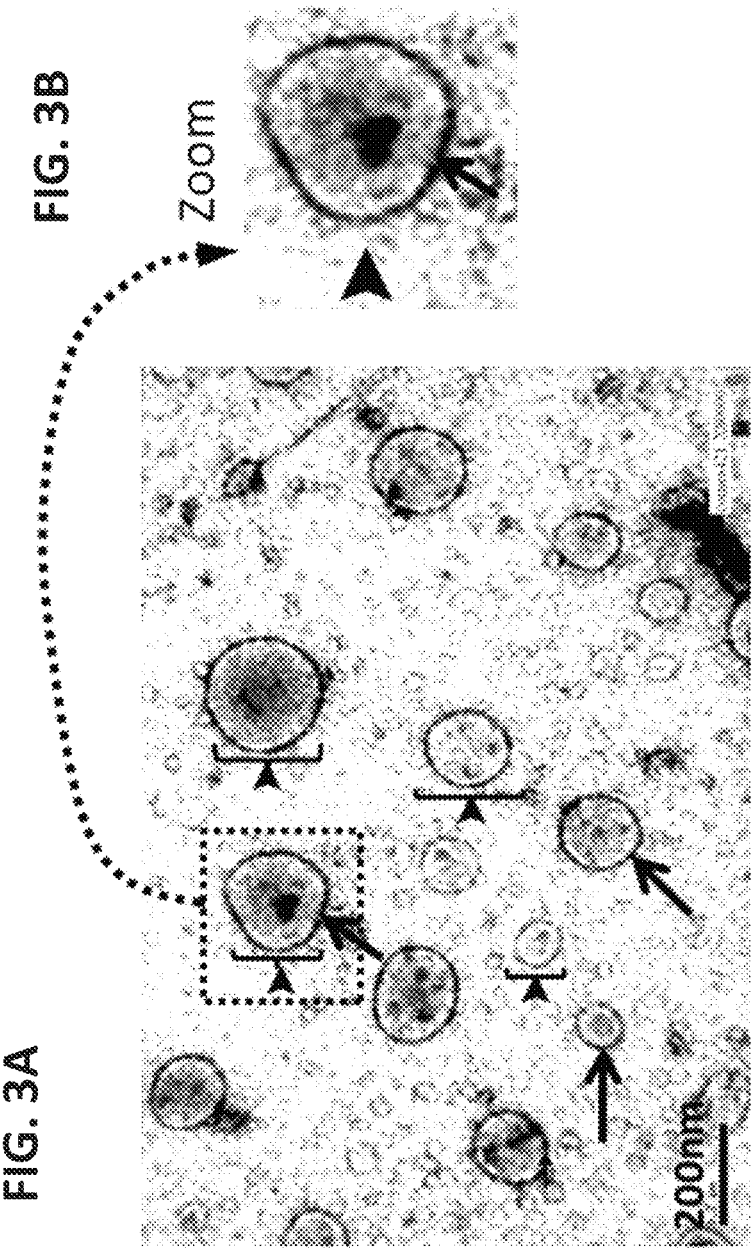
Incorporated from Tendler Y et al., *International Journal of Molecular Medicine* (2015) 36, Suppl. 1, Abstract 463

Incorporated from Tendler Y et al., *International Journal of Molecular Medicine* (2015) 36, Suppl. 1, Abstract 463

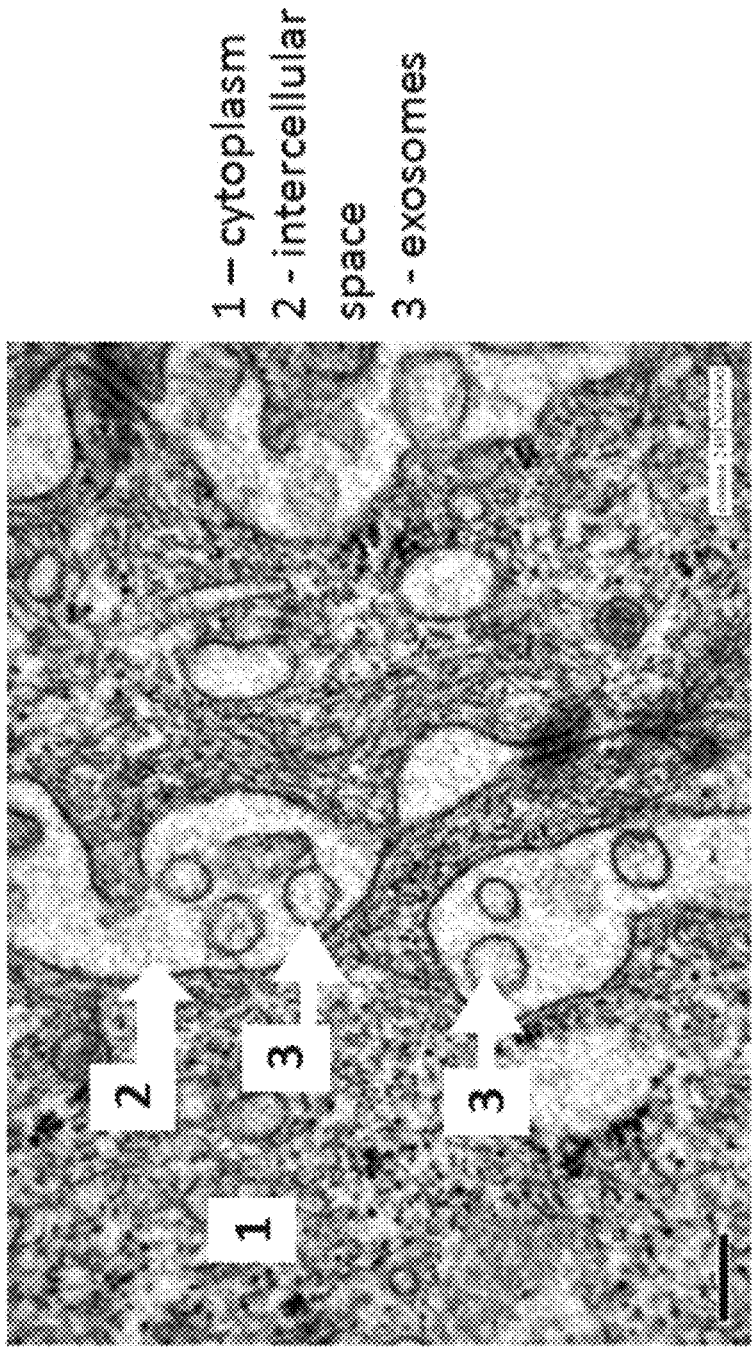

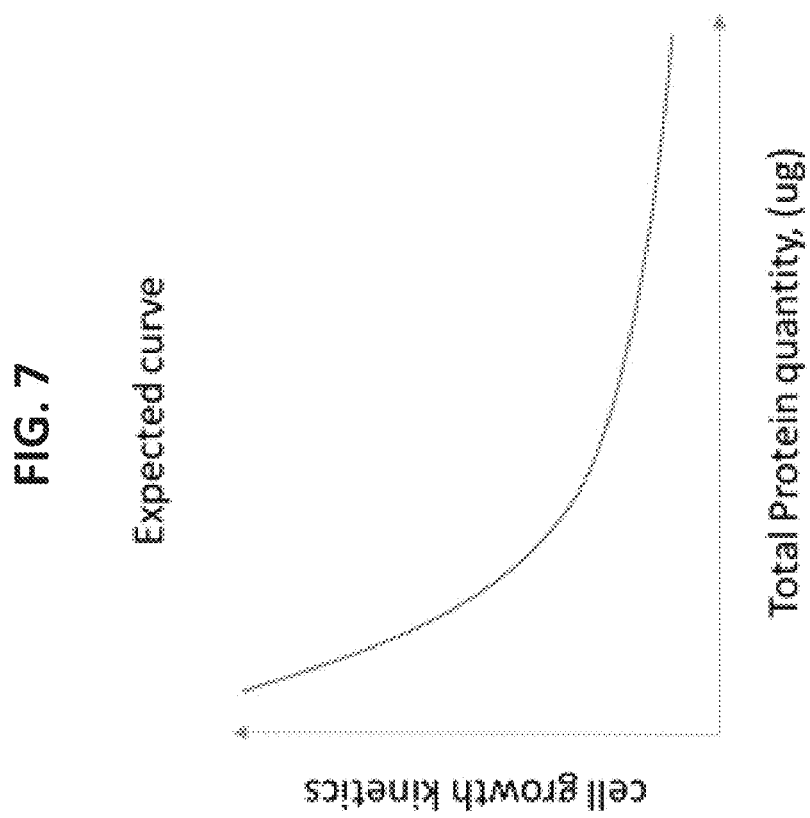

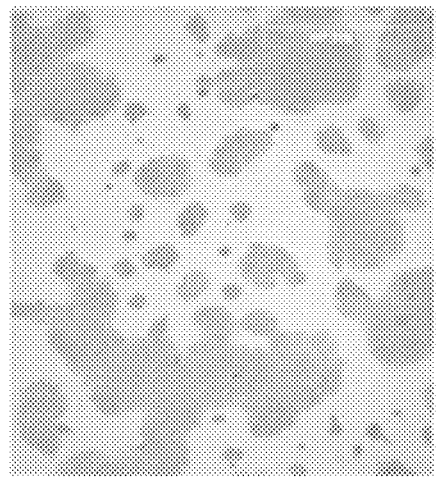
FIG. 8B — Exo_001 50 ul
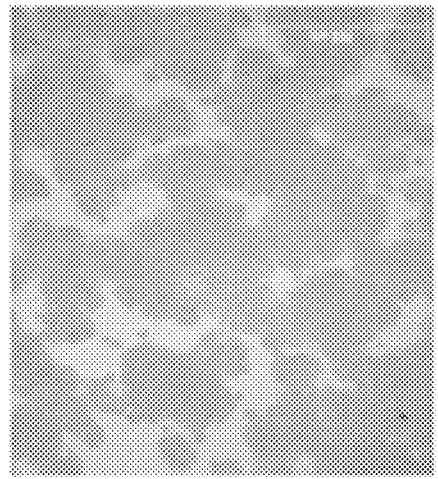
FIG. 8A — Control

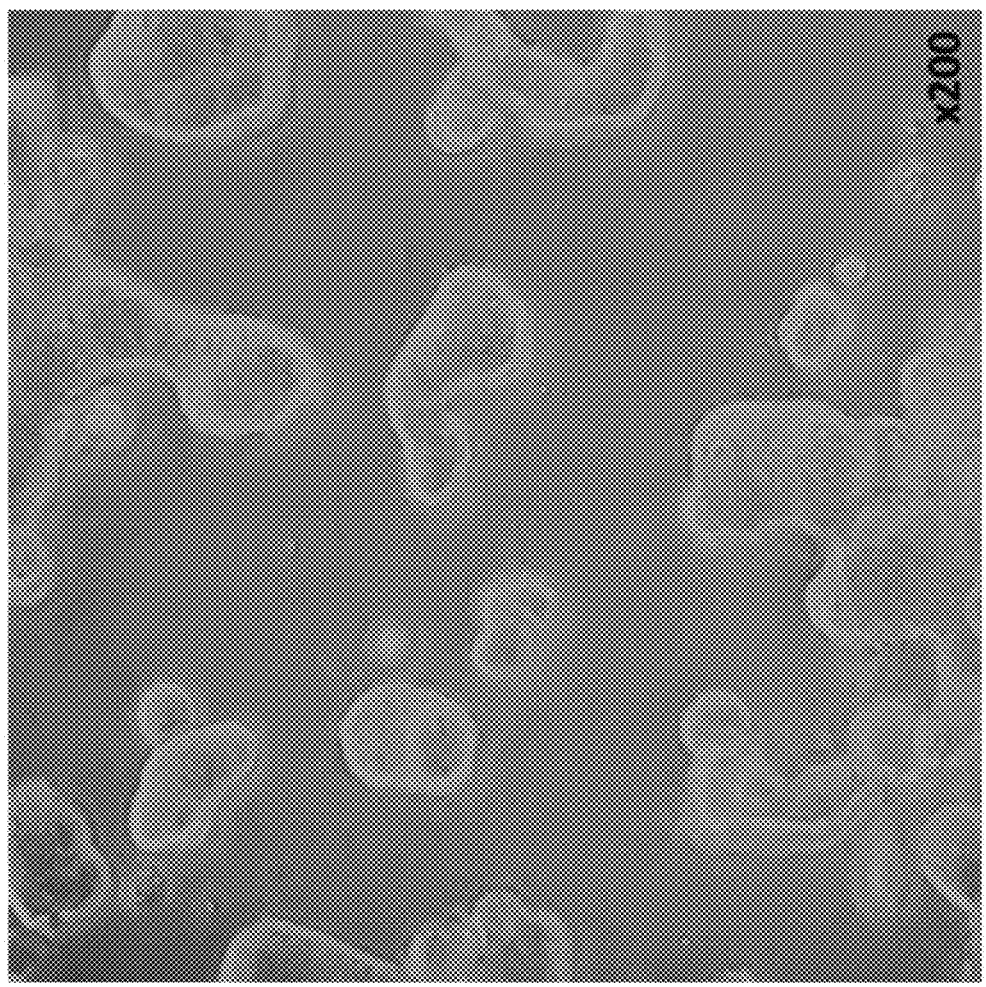
FIG. 12A Treatment

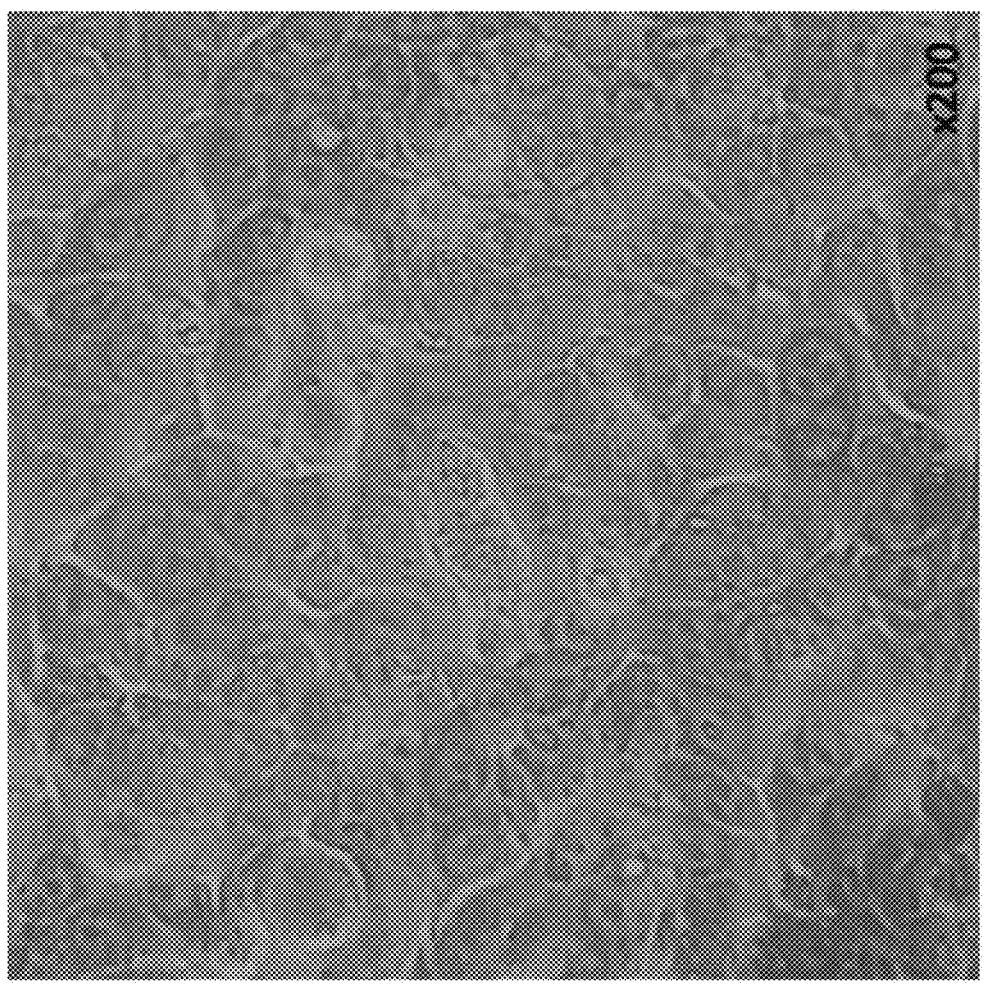
FIG. 12B Control

NATIVE CELL DERIVED VESICLES CONTAINING TUMOR SUPPRESSOR PROTEINS FOR THERAPY

RELATED APPLICATIONS

This application is a National Phase of PCT Patent Application No. PCT/IL2018/050328 having International filing date of Mar. 21, 2018, which claims the benefit of priority under 35 USC §119(e) of U.S. Provisional Patent Application No. 62/474,142 filed on Mar. 21, 2017. The contents of the above applications are all incorporated by reference as if fully set forth herein in their entirety.

FIELD AND BACKGROUND OF THE INVENTION

The present invention, in some embodiments thereof, relates to native cell derived vesicles comprising p53 polypeptide and, more particularly, but not exclusively, to the use of same in treatment.

Extracellular microvesicles can be classified into 3 main classes—(I) microvesicles/microparticles/ectosomes that are produced by outward budding and fission of the plasma membrane, (II) exosomes that are formed within endosomal network and released upon fusion of multi-vesicular bodies (MVB) with the plasma membrane and (III) apoptotic bodies released as blebs of cells undergoing apoptosis.

Over the past few years, evidence has begun to accumulate that the microvesicles serve as signaling payloads containing cell-specific collections of proteins, lipids and genetic material that are transported to other cells where they can alter cell's function and physiology. Exosomes, microvesicles of about 40-200 nm in diameter, have pleiotropic biological functions, including immune response, antigen presentation, intracellular communication, and cell to cell transfer of RNA and proteins. Exosomes are typically formed when cellular compartments known as multivesicular endosomes (MVE) or multivesicular bodies (MVB) bud inward to form small internal vesicles containing proteins, mRNAs and miRNA from the cytoplasm. These internal vesicles are released as exosomes when MVE fuse with the cell membrane or, alternatively fuse with lysosomes.

Recently, experiments with exosomes as means of chemo- and other therapy delivery vehicles were reported, e.g. as means for delivery of drugs, microRNAs, siRNAs, and antigens to target recipient cells in order to treat tumorigenesis or metastasis [Tickner J. A. et al., Front Oncol. (2014) 4: 127; Kim M. S. et al. Nanomedicine: Nanotechnology, Biology and Medicine. (2016) 12(3): 655-664; Yim et al, Nature Communications (2016) 7: 12277].

The p53 gene is a well-characterized tumor suppressor gene. It is one of the major genes responsible for maintenance of genomic stability in vertebrates as well as in Diptera. p53 gene mutations have been found in up to 50% of all human malignancies. In most, if not all, cancers lacking p53 mutation, normal p53 is inactivated by interaction with over expressed MDM2/MDM4 or viral proteins, causing its degradation. Inactivation of p53 functions is an almost universal feature of human cancer cells. Numerous studies have shown that restoring p53 function to p53-deficient cancer cells induces growth arrest and apoptosis [Lane D. et al., Cold Spring Harb Perspect Biol (2010) 2(9): a001222].

In addition to its role as a tumor suppressor, p53 is a nuclear transcription factor which plays a role in apoptosis and cell cycle arrest and senescence. P53 also regulates synthesis and secretion of exosomes from stressed cells. The role of p53 as the "master exosome secretor" was not known until 2006 [Yu X et al., Cancer Res. (2006) 66(9): 4795-801]. Because of its potent role in cancer, p53 is an attractive target for the development of new cancer therapy methods. Gene therapy using wild-type p53 gene, delivered by an adenovirus vector, Gendicine®, is approved for treatment and is now in widespread use in China. Another p53 gene-based cancer therapy, Advexin®, has shown efficacy in a number of clinical trials, both as monotherapy and in combination with radiation and/or chemotherapy agents [Gabrilovich D. I., Expert Opin Biol Ther. (2006) 6(8):823-32]. A number of small molecules that directly or indirectly activate the p53 response have also reached clinics, of which the most advanced are the p53 mdm2 interaction inhibitors—Nutlin and Nutlin 3 [Lane D et al., Cold Spring Harb Perspect Biol, (2010) 2(9): a001222]. Thus, developing methods to safely and efficiently restore p53 activity in tumor cells in vivo has become a key goal in cancer research.

Corneal epithelium is one of the most cancer resistant tissue types. In previous studies unexpectedly high levels of p53 were found in the cytoplasm of corneal epithelial cells [Tendler Y et al., Brain Res Mol Brain Res. (1999) 72: 40-4; Pokroy R. et al., Invest Ophthalmol Vis Sci. (2002) 43: 1736-4; Tendler Y et al. Exp. Eye Res. (2006) 82, 674-681; Tendler Y et al., Int J Mol Med. (2013) 31: 540-6]. The high levels of p53 were accompanied by absence of MDM2.

Following ultraviolet (UV) irradiation, the level of cytoplasmic p53 protein expression was increased while the level of p53 transcriptional activity was not significantly altered. Furthermore, p53 containing exosomes were previously detected in the eye's conjunctival mucin layer [Tendler Y et al., Proceedings of the 20$^{th}$ World Congress on Advances in Oncology and 18$^{th}$ International Symposium on Molecular Medicine (October 2015), Athens, Greece; International Journal of Molecular Medicine (2015) 36, Suppl. 1, Abstract 463].

Trivedi et al. [Oncogenesis (2016) 5, e250] describe modification of tumor cell-derived exosomal content by transfection of cancer cells with wt-p53 and microRNA-125b expressing plasmid DNA. Trivedi et al. further discuss repolarization of macrophages towards a more pro-inflammatory/anti-tumor phenotype following contact with the modified cancer cell-derived exosomes.

U.S. Patent Application Nos. 2010/092524 and 2013/243820 disclose genetically modified cells for generation of exosomes containing one or more antigens (e.g. p53, p63, p'73) and substantially lacking one or more immunosuppressive polypeptides normally found in exosomes (e.g. FasL, PDL-1, PDL-2, B7-H3, B7-H4, and combinations thereof). The cells described further comprise one or more inhibitory polynucleotides that specifically inhibit expression of the one or more immunosuppressive polypeptides. U.S. 20100092524 and U.S. 20130243820 further provide methods of producing the genetically modified exosomes and methods of using the genetically modified exosomes for treating cancers.

Heath uncovered that microvesicles can be used to induce phenotypic changes in cells [Heath, N. An investigation into the role of microvesicles in mutant p53 invasive gain-of-function. PhD thesis, University of Glasgow. (2015)]. According to Heath, cancer cells can turn normal cells into malignant cells by passing their microvesicles to healthy cells, as shown by transfer of mutant p53 protein from mutant p53-expressing cells to p53 null cells. Furthermore, according to Heath, fractionation approaches indicated that the mutant p53 phenotype (mutant p53 protein) was transmitted between cells by a microvesicle vector.

SUMMARY OF THE INVENTION

According to an aspect of some embodiments of the present invention there is provided a method of obtaining cell derived vesicles comprising an active wild-type p53, the method comprising: (i) isolating cell derived vesicles from a biological sample comprising cells; and (ii) treating the cell derived vesicles with a DNA damaging agent, thereby obtaining the cell derived vesicles comprising the active p53.

According to an aspect of some embodiments of the present invention there is provided a method of obtaining cell derived vesicles comprising an active wild-type p53, the method comprising: (i) treating cells with a DNA damaging agent; and (ii) isolating cell derived vesicles from a biological sample comprising the cells, thereby obtaining the cell derived vesicles comprising the active p53.

According to an aspect of some embodiments of the present invention there is provided a proteinaceous preparation comprising cell derived vesicles, the cell derived vesicles comprising an active wild-type p53, wherein the preparation is devoid of intact cells and wherein at least 50% of proteins in the preparation are in the cell derived vesicles, obtainable according to the method of some embodiments of the invention.

According to an aspect of some embodiments of the present invention there is provided a pharmaceutical composition comprising the proteinaceous preparation of some embodiments of the invention and a pharmaceutically acceptable carrier.

According to an aspect of some embodiments of the present invention there is provided a method of treating a disease, disorder or condition associated with a mutant or a nonfunctional p53 protein in a subject in need thereof, the method comprising administering to the subject the pharmaceutical composition of some embodiments of the invention.

According to an aspect of some embodiments of the present invention there is provided an effective amount of the pharmaceutical composition of some embodiments of the invention for use in treating a disease, disorder or condition associated with a mutant or a nonfunctional p53 protein in a subject in need thereof.

According to an aspect of some embodiments of the present invention there is provided a method of inducing apoptosis of a target cell comprising a mutant or a nonfunctional p53 protein, the method comprising contacting the cell with an effective amount of the composition of some embodiments of the invention.

According to an aspect of some embodiments of the present invention there is provided a method of treating a disease, disorder or condition associated with a mutant or a nonfunctional p53 protein in a subject in need thereof, the method comprising administering to the subject a therapeutically effective amount of cell derived vesicles, the cell derived vesicles obtained from cells expressing at least 0.5% endogenous wild-type p53 protein of the total cellular proteins and not expressing recombinant p53 protein.

According to an aspect of some embodiments of the present invention there is provided a therapeutically effective amount of cell derived vesicles obtained from cells expressing at least 0.5% endogenous wild-type p53 protein of the total cellular proteins and not expressing recombinant p53 protein, for use in treating a disease, disorder or condition associated with a mutant or a nonfunctional p53 protein in a subject in need thereof.

According to an aspect of some embodiments of the present invention there is provided a method of inducing apoptosis of a target cell comprising a mutant or a nonfunctional p53 protein, the method comprising contacting the target cell with an effective amount of cell derived vesicles, the cell derived vesicles obtained from cells expressing at least 0.5% endogenous wild-type p53 protein of the total cellular proteins and not expressing recombinant p53 protein.

According to some embodiments of the invention, the cells express at least 0.5% endogenous wild-type p53 protein of the total cellular proteins and do not express recombinant p53 protein.

According to some embodiments of the invention, the active wild-type p53 comprises phosphorylated wild-type p53.

According to some embodiments of the invention, the sample of the subject is obtained prior to the administering to assess that the disease, disorder or condition involves a mutant or a nonfunctional p53 protein.

According to some embodiments of the invention, the method is effected ex vivo.

According to some embodiments of the invention, the method is effected in vivo.

According to some embodiments of the invention, the cell derived vesicles comprise cell secreted vesicles.

According to some embodiments of the invention, the cell derived vesicles have a mean particle diameter of about 20 to about 200 nm.

According to some embodiments of the invention, the cell derived vesicles comprise exosomes.

According to some embodiments of the invention, the cells express endogenous MDM2 polypeptide at a level not exceeding 0.5% of the total cellular proteins.

According to some embodiments of the invention, an outer surface of the cell derived vesicles comprises a heterologous moiety for targeted delivery of the cell derived vesicles to a target cell.

According to some embodiments of the invention, the heterologous moiety is selected from the group consisting of a protein, a peptide and a glycolipid molecule.

According to some embodiments of the invention, the cell derived vesicles are essentially devoid of intact cells.

According to some embodiments of the invention, the cells are cells of an animal tissue.

According to some embodiments of the invention, the animal tissue comprises an eye tissue.

According to some embodiments of the invention, the eye tissue comprises a corneal epithelium tissue or a conjunctiva tissue.

According to some embodiments of the invention, the corneal epithelium tissue comprises corneal epithelial cells.

According to some embodiments of the invention, the animal tissue is selected from the group consisting of a corneal epithelium, a conjunctiva, an epidermis, a testicle, an epithelium of small intestines and a brain tissue.

According to some embodiments of the invention, the cells are selected from the group consisting of corneal epithelium cells, intestinal epithelial cells, conjunctival cells, goblet cells, skin epithelial cells, skin fibroblasts, cerebellum cells, hippocampus cells, hypothalamus cells, pons cells, thalamus cells and upper cerebral spine cells.

According to some embodiments of the invention, the cells are healthy cells.

According to some embodiments of the invention, the cells are genetically non-modified cells.

According to some embodiments of the invention, the cells are genetically modified cells.

According to some embodiments of the invention, the cells have been treated with a MDM2 inhibitor.

According to some embodiments of the invention, the cells have been treated with a DNA damaging agent to activate the p53 protein.

According to some embodiments of the invention, the DNA damaging agent is selected from the group consisting of a UV irradiation, a gamma irradiation, a chemotherapy, an oxidative stress, hypoxia, nutrient deprivation.

According to some embodiments of the invention, the DNA damaging agent comprises UV irradiation.

According to some embodiments of the invention, the target cell comprises a cancer cell.

According to some embodiments of the invention, the cancer cell is a cell of a solid tumor or metastasis.

According to some embodiments of the invention, the cancer cell is a cell of a hematologic malignancy.

According to some embodiments of the invention, the disease, disorder or condition associated with a mutant or a nonfunctional p53 protein comprises cancer.

According to some embodiments of the invention, the cancer is a solid tumor or metastasis.

According to some embodiments of the invention, the cancer is a hematologic malignancy.

According to some embodiments of the invention, the solid tumor or metastasis is selected from the group consisting of an ovarian cancer, a cervical cancer, a vaginal cancer, a vulvar cancer, an anal cancer, a penile cancer, a breast cancer, an endometrial cancer, a head and neck cancer, a colon cancer, a colorectal cancer, a prostate cancer, a lung cancer, a melanoma, a pancreatic cancer, a liver cancer and a splenic cancer.

According to some embodiments of the invention, the hematologic malignancy comprises a leukemia or lymphoma.

According to some embodiments of the invention, the administering comprises a route selected from the group consisting of intravenous, intra-arterial, intratumoral, subcutaneous, intramuscular, transdermal and intraperitoneal.

According to some embodiments of the invention, the subject is a human subject.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-B are photographs illustrating the p53 protein expression in mouse cornea. P53 positive staining is seen in the cytoplasm of corneal epithelial cells. Negative staining is in epithelial cells nucleus (incorporated from Tendler Y et al. (2015), supra).

Figure 2A:
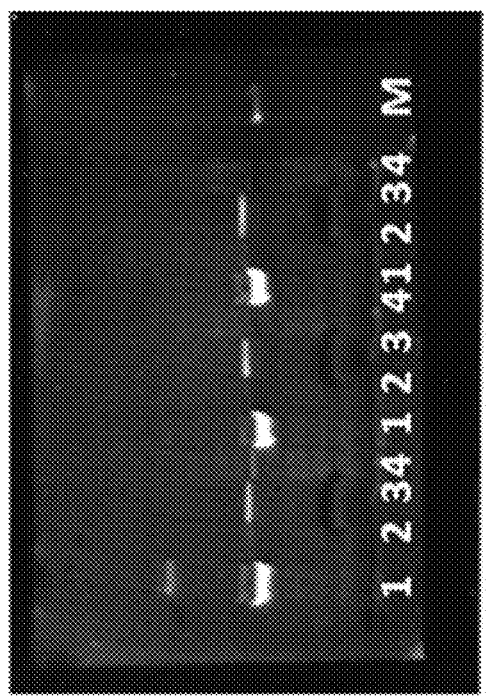
Figure 2B:
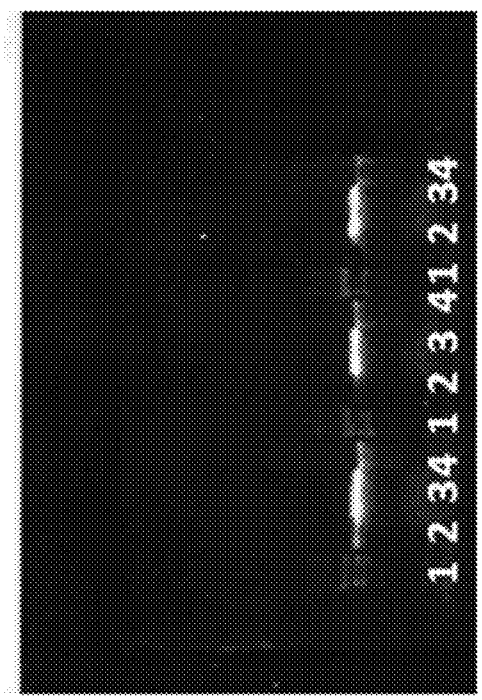

FIGS. 2A-B are photographs illustrating Western Blot Analysis of MDM2-60 cleavage product: 1—cornea, 2—iris, 3—lens, 4—retina and M—p53 positive control. Of note, in cornea, a strong positive p53 (1, top blot) and negative MDM2 (1, bottom blot) is observed. Furthermore, in normal eye, MDM2 protein is found in the lens, iris, and retina while in the normal corneal epithelium MDM2 protein is completely absent (incorporated from Tendler Y et al. (2015), supra).

Figure 3C:
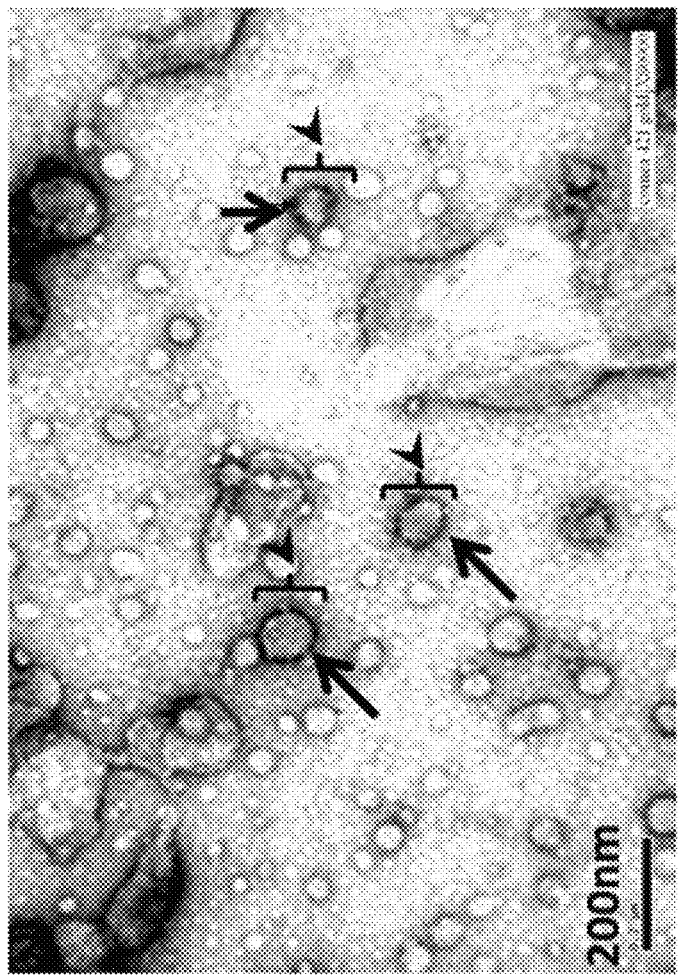

FIGS. 3A-C are photographs illustrating an electron micrograph of p53 containing cell derived vesicles in tear film. The first antibody used was Mab 421 and the secondary antibody uses was gold conjugated anti-mouse IgG. Arrow heads denote 50-200 nm sized exosomes. Solid arrows denote 10 nm diameter gold particles. Magnification 80 K and scale bar 200 nm. FIGS. 3A-B—tear film of rat; FIG. 3C—human tear film (incorporated from Tendler Y et al. (2015), supra).

FIG. 4 is a photograph illustrating cell derived vesicles in the intercellular space of mouse corneal epithelium. Magnification 60 K (incorporated from Tendler Y et al. (2015), supra).

Figure 5C:
Figure 5B:
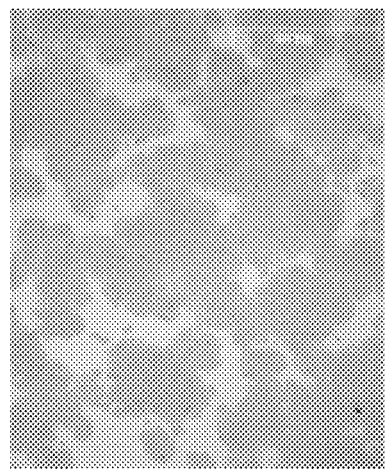
Figure 5A:
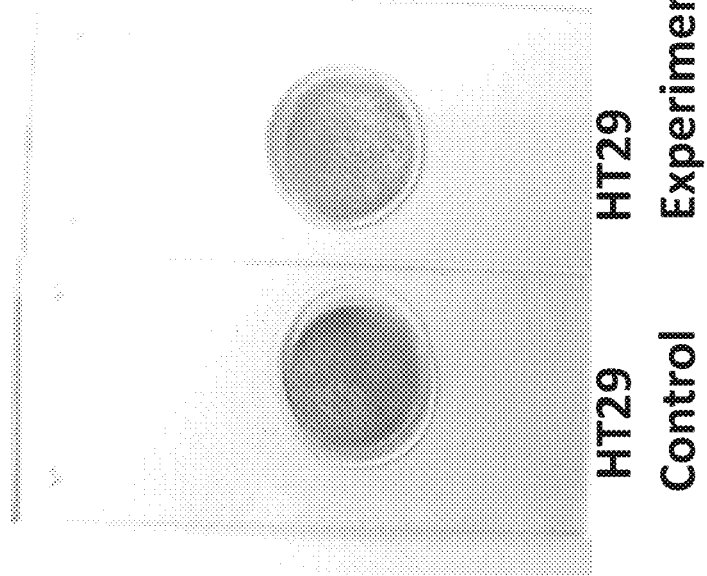

FIGS. 5A-C are photographs illustrating HT-29 cells 72 hours after treatment with cell derived vesicles. Group 1 (control): HT-29 cells were maintained as per manufacturer's instruction. Group 2 (experiment): HT-29 cells were treated with cell derived vesicles derived from a primary culture of rat corneal epithelial cells induced by UV irradiation. FIG. 5A—micrograph of Group 1 (control) and Group 2 (experiment). FIG. 5B—micrograph of Group 1 (control), Magnification ×100. FIG. 5C—micrograph of Group 2 (experiment), Magnification ×100.

Figure 6B:
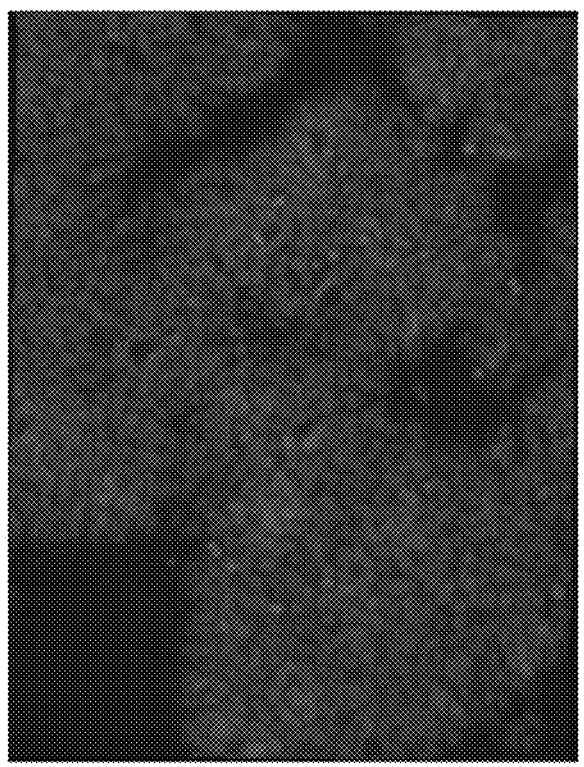
Figure 6A:

FIGS. 6A-B are photographs illustrating apoptosis of HT-29 cells after treatment with p53-containing cell derived vesicles (derived from a primary culture of rat corneal epithelial cells induced by UV irradiation, i.e. EXO_001 agent, as described in detail in the 'materials and experimental procedures' section herein below). Apoptotic cells stained with anti-Annexin V-FITC (green; appears light in the black and white image). Nucleus—PI (red; appears dark in the black and white image). FIG. 6A—Group 1 (experiment) Magnification ×630. FIG. 6B—Group 2 (control) shows no evidence of apoptotic cells.

Figure 6C:
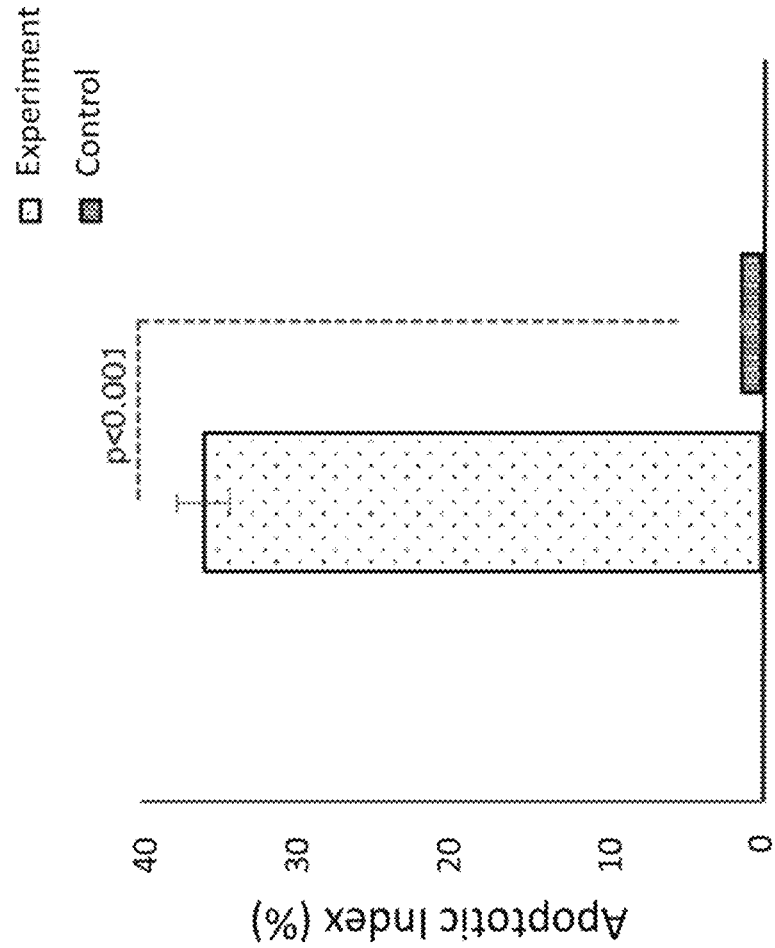

FIG. 6C is a graph presenting apoptotic index (AI) of HT-29 malignant cells treated with 100 µl EXO_001 derived from chicken corneal epithelial cells (as described in detail in the 'materials and experimental procedures' section herein below).

FIG. 7 is a graph illustrating a dose dependent effect of cell derived vesicles on malignant cell growth kinetics.

FIGS. 8A-B are photographs illustrating HT-29 malignant cells growth kinetics treated with EXO_001 agent derived from a primary culture of rat corneal epithelial cells (as described in detail in the 'materials and experimental procedures' section herein below).

Figures 9A, 9B:
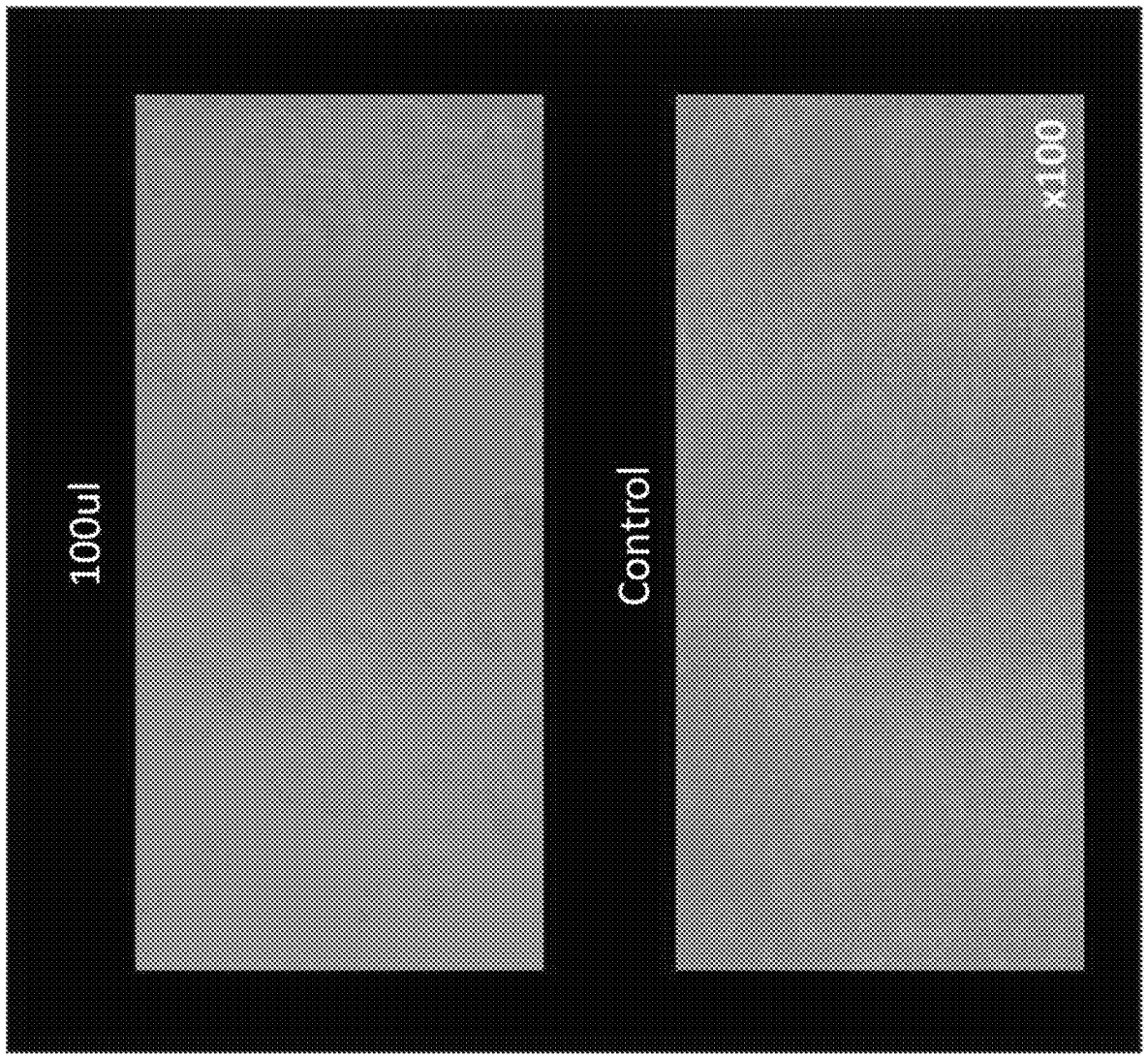

FIGS. 9A-B are photographs illustrating HT-29 malignant cells growth kinetics treated with EXO_002 agent derived from chicken corneal epithelial cells (as described in detail in the 'materials and experimental procedures' section herein below). Magnification ×100. Shown are cells 24 hours after the beginning of treatment. FIG. 9A: cells treated with 100 μl EXO_002. FIG. 9B: control.

Figures 10A, 10B:
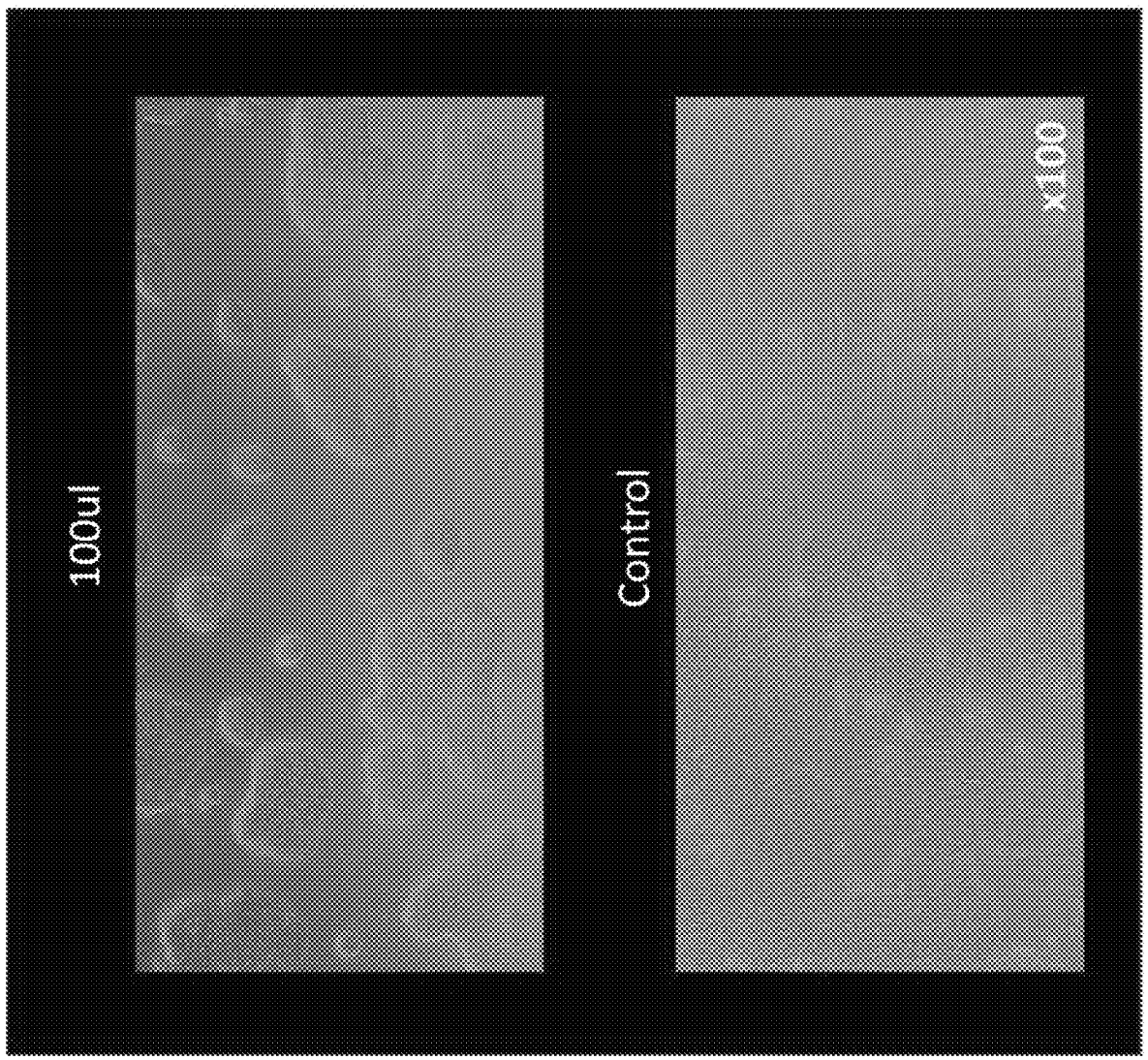

FIGS. 10A-B are photographs illustrating HT-29 malignant cells growth kinetics treated with EXO_002 agent derived from chicken corneal epithelial cells (as described in detail in the 'materials and experimental procedures' section herein below). Magnification ×100. Shown are cells 48 hours after the beginning of treatment. FIG. 10A: cells treated with 100 μl EXO_002. FIG. 10B: control.

Figures 11A, 11B:
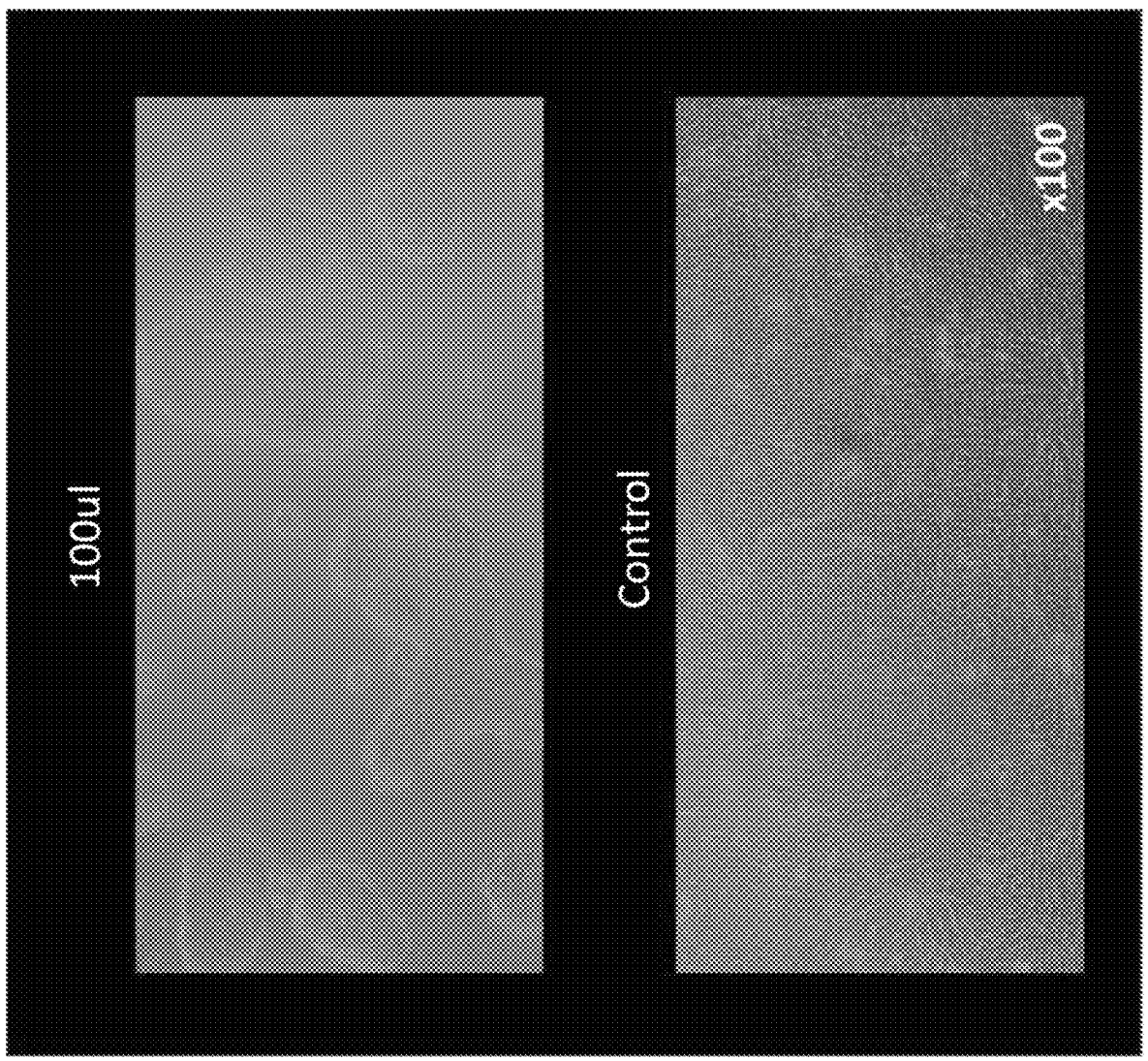

FIGS. 11A-B are photographs illustrating HT-29 malignant cells growth kinetics treated with EXO_002 agent derived from chicken corneal epithelial cells (as described in detail in the 'materials and experimental procedures' section herein below). Magnification ×100. Shown are cells 72 hours after the beginning of treatment. FIG. 11A: cells treated with 100 μl of EXO_002. FIG. 11B: control.

FIGS. 12A-B are photographs illustrating HT-29 malignant cells growth kinetics treated with EXO_002 agent derived from chicken corneal epithelial cells and stored for 1 year (as described in detail in the 'materials and experimental procedures' section herein below). Shown are cells 24 hours after beginning of the treatment. Magnification ×200. FIG. 12A: cells treated with 100 μl of EXO_002. FIG. 12B: control.

Figure 13:
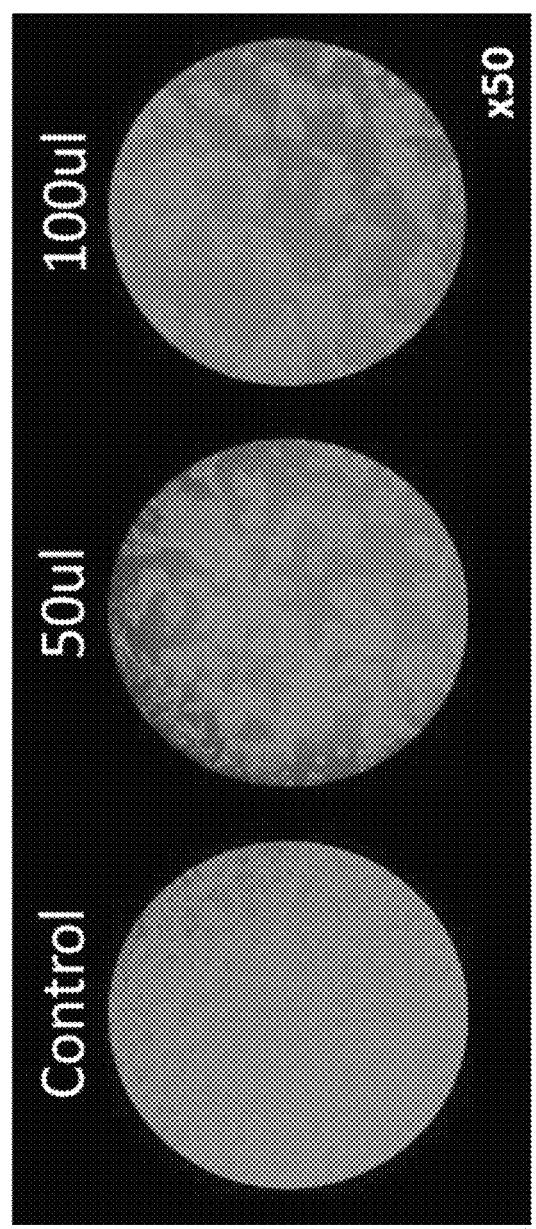

FIG. 13 is a photograph illustrating dose effect of EXO_002 agent derived from chicken corneal epithelial cells (as described in detail in the 'materials and experimental procedures' section herein below) on HT-29 malignant cells growth kinetics. Left: control. Middle: cells treated with 50 μl EXO_002. Right: cells treated with 100 μl EXO_002. Magnification ×50.

Figure 14A:
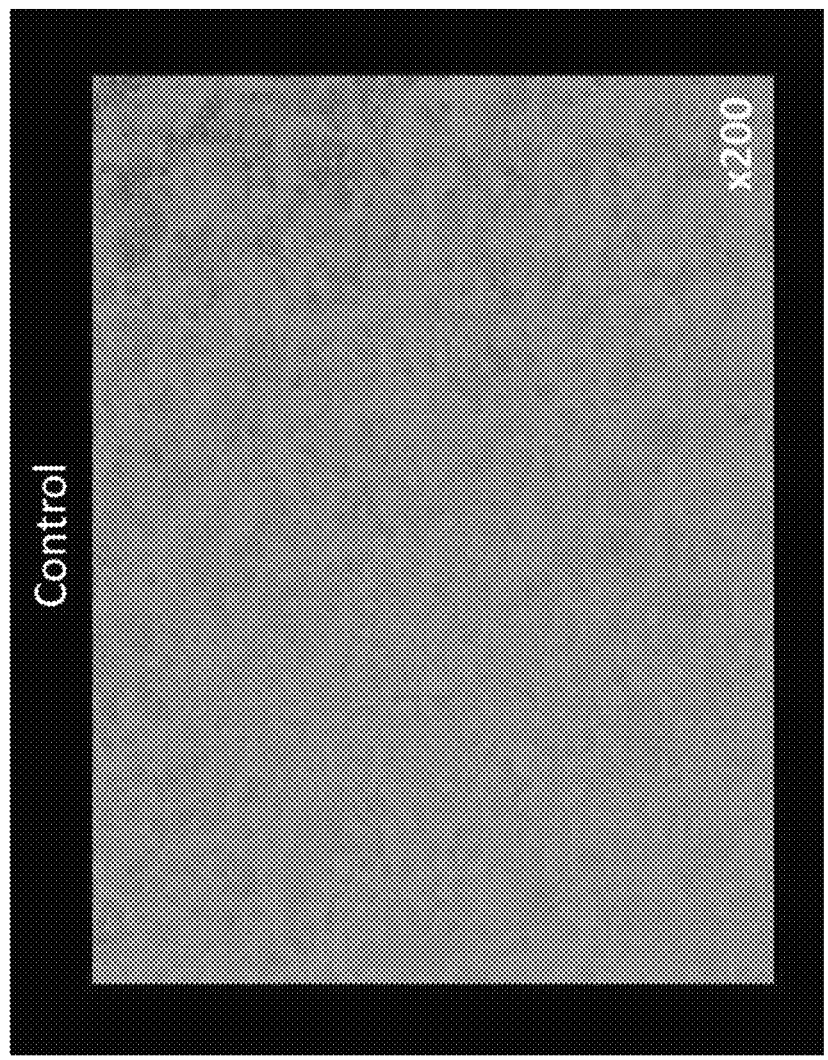
Figure 14B:
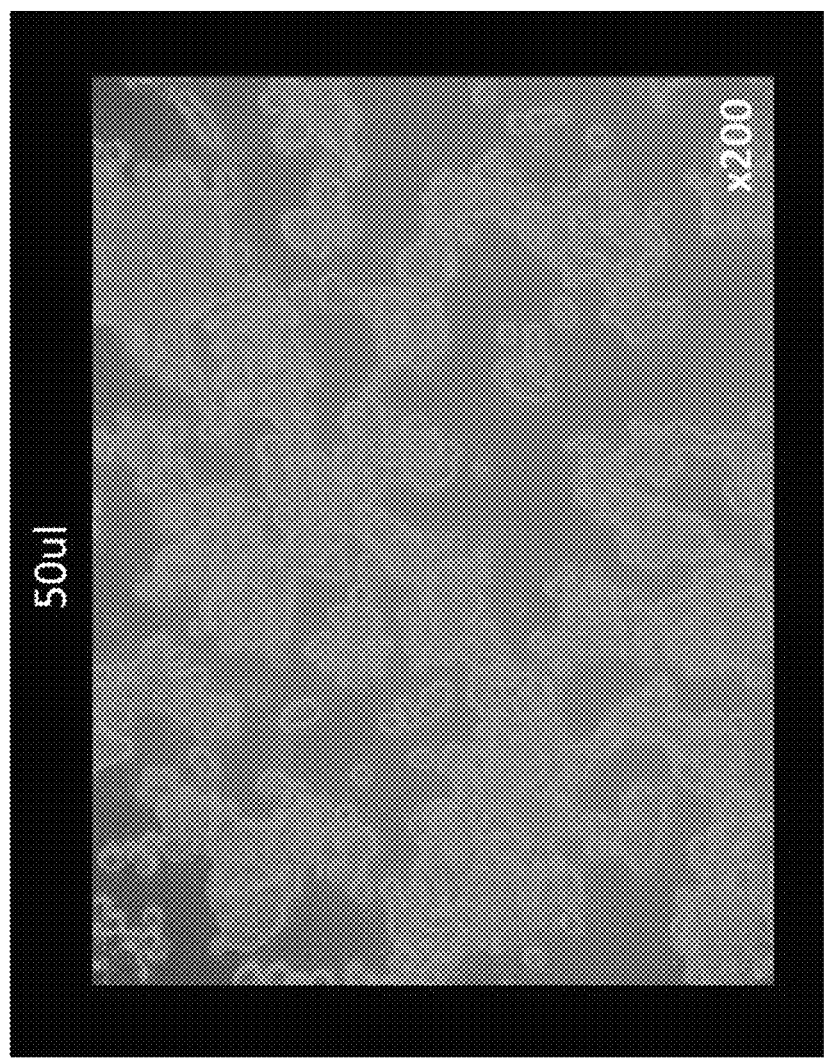
Figure 14C:
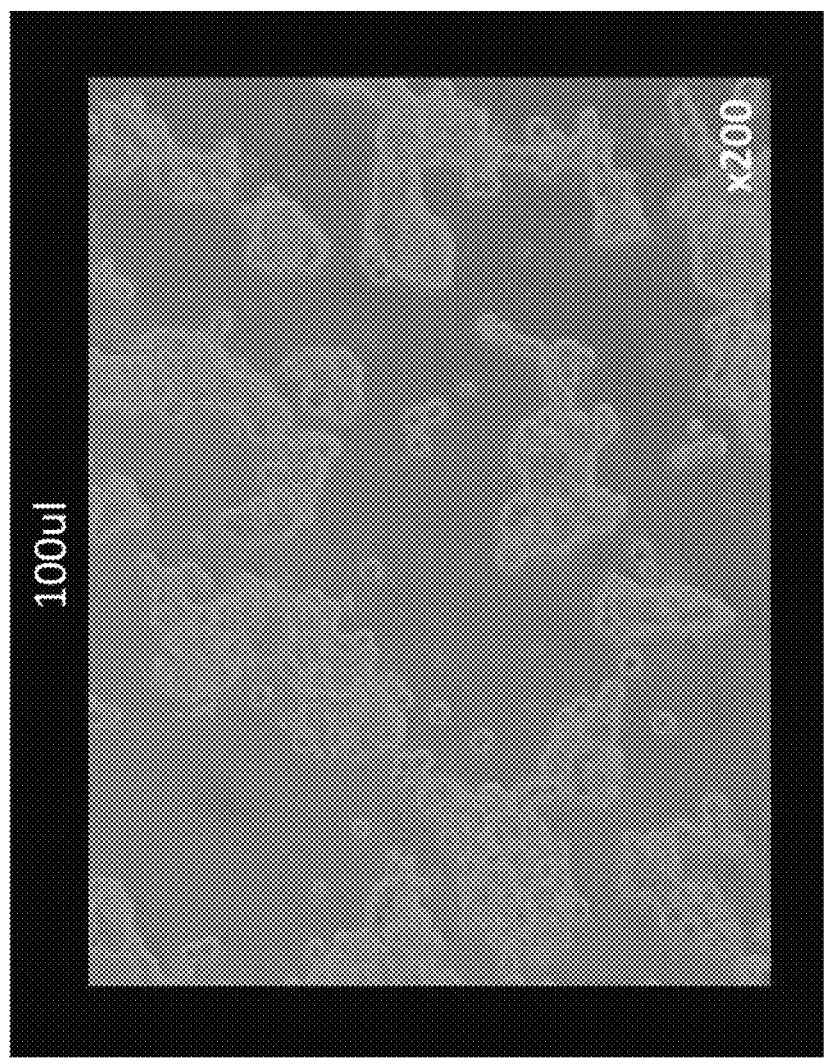

FIGS. 14A-C are photographs illustrating dose effect of EXO_002 agent derived from chicken corneal epithelial cells (as described in detail in the 'materials and experimental procedures' section herein below) on HT-29 malignant cells growth kinetics. Magnification ×200. FIG. 14A: control. FIG. 14B: cells treated with 50 μl EXO_002. FIG. 14C: cells treated with 100 μl EXO_002.

Figures 15A, 15B:
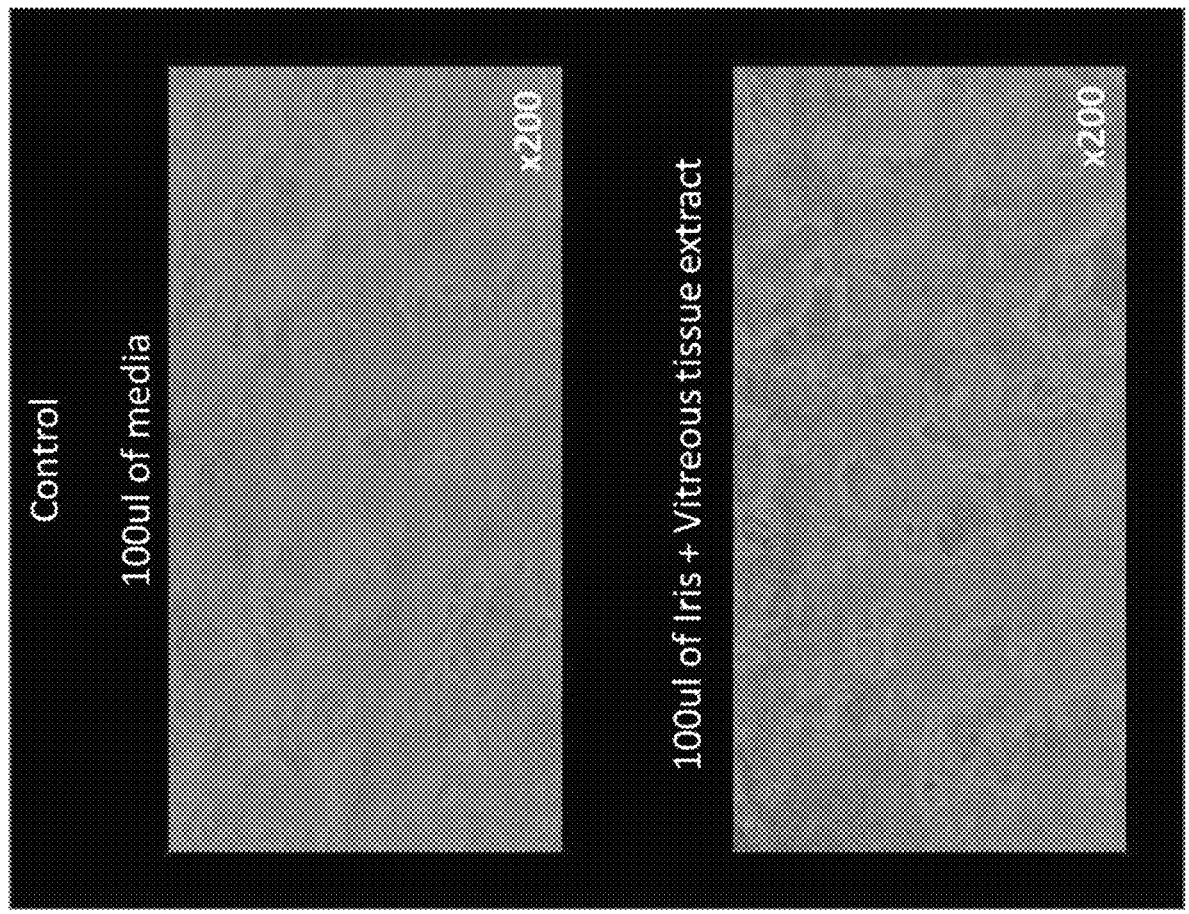

FIGS. 15A-B are photographs illustrating the specificity of EXO_002 (as described in detail in the 'materials and experimental procedures' section herein below) effect on HT-29 malignant cells growth kinetics. Control HT-29 malignant cells treated with 100 μl cell culture media (FIG. 15A) and control treated with vitreous and iris tissue extract (FIG. 15B). Magnification ×200.

Figures 16A, 16B:
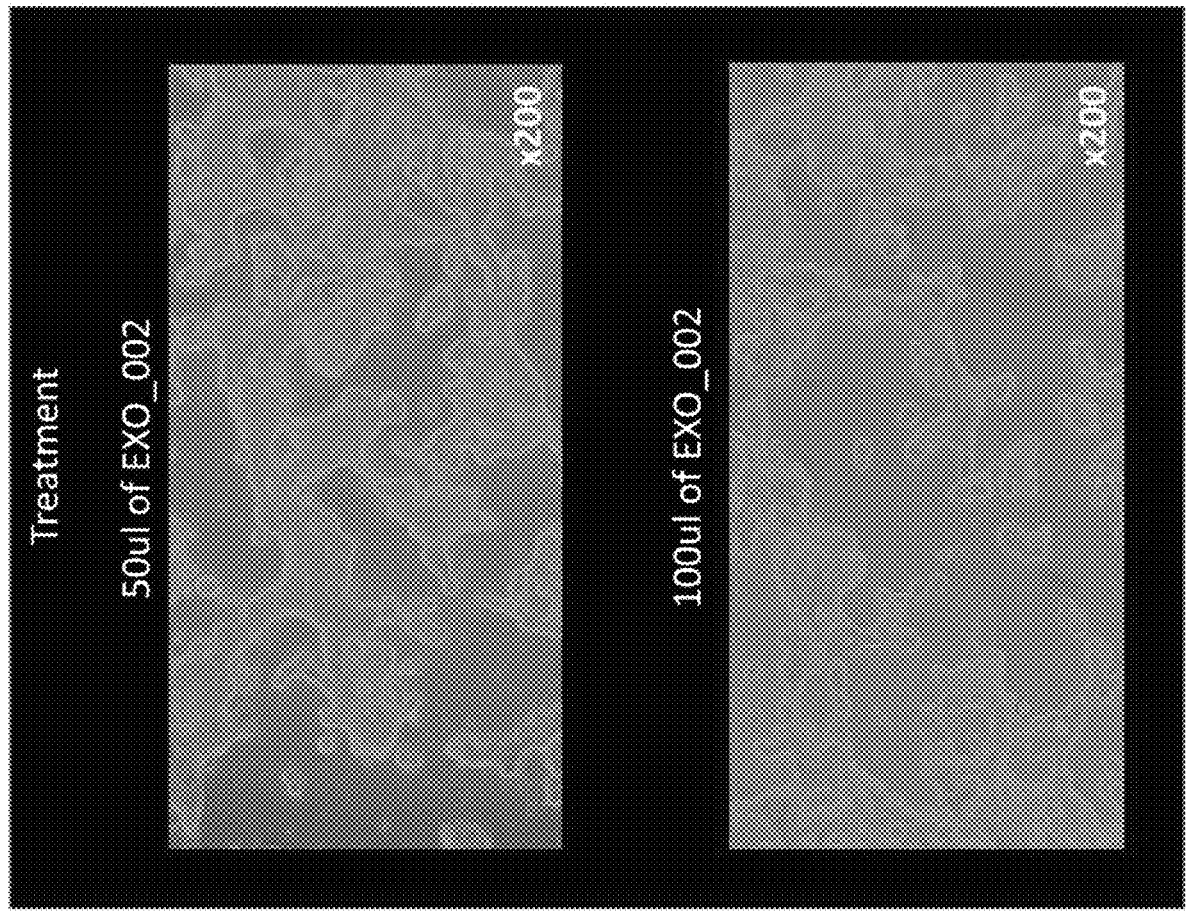

FIGS. 16A-B are photographs illustrating the specificity of EXO_002 (as described in detail in the 'materials and experimental procedures' section herein below) effect on HT-29 malignant cells growth kinetics HT-29 malignant cells treated with 50 μl EXO_002 (FIG. 16A) and cells treated with 100 μl EXO_002 (FIG. 16B). Magnification ×200.

DESCRIPTION OF SPECIFIC EMBODIMENTS OF THE INVENTION

The present invention, in some embodiments thereof, relates to native cell derived vesicles comprising p53 polypeptide and, more particularly, but not exclusively, to the use of same in treatment.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Extracellular microvesicles, including exosomes, serve as signaling payloads containing cell-specific collections of proteins, lipids and genetic material that are transported to other cells where they can alter the cells' function and physiology. Recent experiments with exosomes as means of chemo- and other therapy delivery vehicles were reported, e.g. as means for delivery of drugs, microRNAs, siRNAs, and antigens to target recipient cells in order to treat tumorigenesis or metastasis.

The p53 gene is a well-characterized tumor suppressor gene. It is one of the major genes responsible for maintenance of genomic stability in vertebrates as well as in Diptera. p53 gene mutations and over-expression have been found in up to 50% of all human malignancies.

Previous studies found high levels of p53 in the cytoplasm and microparticles of corneal epithelium, one of the most cancer resistant tissue types, which were accompanied by the absence of MDM2. Following ultraviolet (UV) irradiation, the level of cytoplasmic p53 protein expression was increased while the level of p53 transcriptional activity was not significantly altered.

The present inventors have uncovered that native p53-containing cell derived vesicles obtained from p53-high expressing cells (e.g. corneal epithelial cells) can be used for the treatment of diseases associated with mutant or nonfunctional p53 protein e.g. hyperproliferative diseases, such as cancer. Accordingly, the p53 containing cell derived vesicles are targeted to the diseased cells and used for delivering active p53 proteins thereto, thereby restoring p53 activity in the diseased cell (e.g. tumor cells). The native p53-containing cell derived vesicles can be used as is or in combination with other forms of therapy for hyperproliferative diseases (e.g. cancer) such as chemotherapy or radiotherapy.

Thus, according to one aspect of the present invention there is provided a proteinaceous preparation comprising cell derived vesicles, the cell derived vesicles comprising an active wild-type p53, wherein the preparation is devoid of intact cells and wherein at least 50% of proteins in the preparation are in the cell derived vesicles.

As used herein the terms "p53" or "p53 protein" refer to the tumor suppressor protein p53 (also referred to Tumor Protein P53 or TP53, Cellular tumor antigen p53, Antigen NY-CO-13, Phosphoprotein p53). p53 generally functions as a nuclear protein (transcription factor) that plays an essential role in the regulation of cell cycle, specifically in the transition from G0 to G1. Thus, p53 is a DNA-binding protein containing DNA-binding, oligomerization and transcription activation domains. It is postulated to bind as a tetramer to a p53-binding site and activate expression of downstream genes that inhibit growth and/or invasion, and hence acting, in its wild-type form, as a tumor suppressor.

According to one embodiment, the p53 protein is a human p53.

Exemplary human p53 proteins include, but are not limited to, those listed under GenBank accession nos.

NP_000537.3, NP_001119584.1, NP_001119585.1, NP_001119586.1, NP_001119587.1, NP_001119588.1 and NP_001119589.1.

According to one embodiment, the p53 protein is an animal p53 protein (e.g. farm animal).

According to one embodiment, the p53 protein is a chicken (Gallus Gallus) p53 protein.

Exemplary chicken p53 proteins include, but are not limited to, those listed under GenBank accession no. NP_990595.1.

According to one embodiment, the p53 protein is a swine (Sus Scrofa) p53 protein.

Exemplary swine p53 proteins include, but are not limited to, those listed under GenBank accession no. NP_998989.3.

According to one embodiment, the p53 protein is a cattle (Bos Taurus) p53 protein. Exemplary cattle p53 proteins include, but are not limited to, those listed under GenBank accession no. NP_776626.1.

According to one embodiment, the p53 protein is a sheep (Ovis Aries) p53 protein. Exemplary sheep p53 proteins include, but are not limited to, those listed under GenBank accession nos. XP_011954275.1, XP_011954277.1, XP_004017979.1 and XP_011954276.1. According to one embodiment, the p53 protein is a mouse (Mus Musculus) p53 protein.

Exemplary mouse p53 proteins include, but are not limited to, those listed under GenBank accession nos. NP_001120705.1 and NP_035770.2.

According to one embodiment, the p53 protein is of an elephant (Loxodonta Africana) p53 protein. Exemplary elephant p53 proteins include, but are not limited to, those listed under GenBank accession nos. G3UI57, G3UJ00, G3UK14, G3UHY3, G3TS21, G3U6D1, G3T035, G3U6U6, G3UDE4, G3ULT4, G3UAZ0 and G3UHE5.

According to one embodiment, the p53 protein is of a goat p53 protein.

According to one embodiment, the active wild-type p53 protein comprises a phosphorylated wild-type p53 protein.

According to one embodiment, phosphorylation of p53 is at the N- and/or C-terminal domain of p53. For example, p53 can be phosphorylated at serine (e.g. serine 15, 33, 37 or 392) or threonine (e.g. threonine 18) residues within the N- and/or C-terminal regions of the protein. Phosphorylation can be detected by any method known in the art, such as by Western Blot analysis.

According to one embodiment, phosphorylation of p53 stabilizes and/or activates and/or prolongs the half-life and/or increases the levels of p53 protein in a cell. Thus, for example, phosphorylation of p53 prolongs the half-life of p53 from several minutes (e.g. from about 1, 2, 5, 10, 20, 30, 40, 50 or 60 minutes) to several hours (e.g. to about 0.5, 1, 2, 3, 5, 10, 15, 20, 25, 30, 40, 50 or 60 hours). According to one embodiment, phosphorylation of p53 prolongs the half-life of p53 by several-fold, such as by about 2, 3, 4, 5, 6, 7, 8, 9 or 10 times.

According to some embodiments of the invention, treating with a DNA damaging agent phosphorylates p53. DNA damaging agents are discussed in detail below.

The terms "mutant p53 protein" or "nonfunctional p53 protein" as used herein may interchangeably be used and are directed to a p53 protein incapable of executing at least one of wild-type p53 biological activities in a cell. In some embodiments nonfunctional p53 is mutated. In other embodiments nonfunctional p53 comprises a wild-type p53 amino acid sequence (e.g. as set forth in GenBank Accession nos. NP_000537.3, NP_001119584.1, NP_001119585.1, NP_001119586.1, NP_001119587.1, NP_001119588.1 and NP_001119589.1). In some embodiments, a mutant or non-functional p53 protein cannot bind its target site. In some embodiments, a mutant or nonfunctional p53 protein is mutated at the DNA binding domain (DBD) region. In some embodiments, a mutant or nonfunctional p53 protein is misfolded in an inactive conformation.

For example, a mutant or nonfunctional p53 can be a result of a gene mutation (e.g. point mutation, missense mutation) in which one or more nucleotides is substituted by another nucleotide. The p53 mutations are very diverse in their locations within the p53 coding sequence, and the different mutations may affect the stability (e.g. thermodynamic stability) of the p53 protein. However, regardless of the type of mutation, the mutations may result in the protein's loss of DNA binding ability in a sequence-specific manner and in activation of transcription of p53-regulated genes (e.g. genes involved in DNA repair, cell cycle, autophagy, apoptosis, etc.), and hence cause the loss of tumor suppressor activity.

Exemplary p53 protein mutations include, but are not limited to, R175H, V143A, R249S, R273H, R280K, P309S, P151S, P151H, C176S, C176F, H179L, Q192R, R213Q, Y220C, Y220D, R245S, R282W, D281G, S241F, C242R, R248Q, R248W, D281G, R273C and V274F.

Determining that a p53 protein is active can be carried out using any method known in the art, such as but not limited to, Enzyme linked immunosorbent assay (ELISA), Western blot, Radio-immunoassay (RIA), Fluorescence activated cell sorting (FACS), Immunohistochemical analysis, In situ activity assay and In vitro activity assays. Similarly, these methods can be used to assess a mutant or nonfunctional p53 proteins. Additional methods are provided herein below.

The term "cell derived vesicles" as used herein refers to externally released vesicles originating from the endosomal compartment of cells.

The cell derived vesicles of the invention have cytoplasmic content which comprises p53 and is entrapped in a cell membrane. The cell derived vesicles of the invention include membrane markers of the cell.

According to one embodiment, the cell derived vesicles are cell secreted vesicles.

According to one embodiment, the cell derived vesicles include exosomes.

For example, exosomes are formed by invagination and budding from the limiting membrane of late endosomes. They accumulate in cytosolic multivesicular bodies (MVBs) from where they are released by fusion with the plasma membrane. Alternatively, vesicles similar to exosomes (though somewhat larger, often called 'microvesicles') can be released directly from the plasma membrane. Depending on the cellular origin, cell derived vesicles harbor biological material including e.g. nucleic acids (e.g. RNA or DNA), or cytoplasmic content including proteins, peptides, polypeptides, antigens, lipids, carbohydrates, and proteoglycans. For example, various cellular proteins can be found in cell derived vesicles including MHC molecules, tetraspanins, adhesion molecules and metalloproteinases.

Cell derived vesicles (e.g. cell secreted vesicles) typically have a particle size (e.g. diameter) of about 10, 20, 30, 40, 50, 60, 70, 80, 90, 100, 150, 200, 250 300, 500 or 1000 nm.

According to one embodiment, the cell derived vesicles (e.g. cell secreted vesicles) have a particle size (e.g. diameter) of about 10-1000 nm, about 10-750 nm, about 10-500 nm, about 10-250 nm, about 10-100 nm, about 10-50 nm, about 10-25 nm, about 10-20 nm, about 20-1000 nm, about 20-750 nm, about 20-500 nm, about 20-250 nm, about 20-100 nm, about 20-50 nm, about 50-1000 nm, about 50-750 nm, about 50-500 nm, about 50-100 nm, about 100-1000 nm, about 100-750 nm, about 100-500 nm, about 100-250 nm, about 200-1000 nm, about 200-750 nm, about 200-500 nm, or about 200-250 nm.

According to one embodiment, the cell derived vesicles (e.g. cell secreted vesicles) have a particle size (e.g. diameter) of no more than about 1000 nm, 750 nm, 500 nm, 250 nm, 200 nm, 150 nm, 100 nm, 50 nm, 25 nm, 20 nm or 10 nm.

According to one embodiment, the cell derived vesicles (e.g. cell secreted vesicles) have a particle size (e.g. diameter) of about 20-200 nm (e.g. about 30-100 nm).

The term "endogenous" as used herein refers to any polynucleotide or polypeptide which is naturally expressed within the cells from which the cell derived vesicles are obtained.

As used herein, the phrase "exogenous" refers to a polynucleotide or polypeptide which may not be naturally expressed within the cells from which the cell derived vesicles are obtained.

According to one embodiment, the cell derived vesicles contain at least about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10% or more endogenous wild-type p53 protein (i.e., p53 protein not added exogenously i.e., resulting from gene expression in the cell source) of the total cellular proteins.

According to a specific embodiment, the cell derived vesicles contain an amount of at least 0.5% endogenous wild-type p53 protein of the total proteins in the cell derived vesicles.

According to one embodiment, the cell derived vesicles contain endogenous MDM2 polypeptide at a level not exceeding 0.01%, 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10% of the total cellular proteins.

According to a specific embodiment, the cell derived vesicles contain endogenous MDM2 polypeptide at a level not exceeding 0.5% of the total proteins in the cell derived vesicles.

As used herein the term "MDM2" or "MDM2 polypeptide" refers to the Mouse Double Minute 2, Human Homolog Of. MDM2 generally functions as a p53-binding protein which negatively regulates p53. Accordingly, under normal conditions, MDM2 maintains low intracellular levels of p53 by targeting p53 to the proteasome for rapid degradation and inhibits p53's transcriptional activity.

According to one embodiment, the MDM2 polypeptide is a human MDM2 polypeptide. Exemplary human MDM2 polypeptides include, but are not limited to, those listed under GenBank accession nos. NP_001138809.1, NP_001138811.1, NP_001138812.1, NP_001265391.1 and NP_002383.2.

According to one embodiment, the MDM2 polypeptide is an animal MDM2 polypeptide (e.g. a farm animal e.g. cattle, sheep, goat, chicken, pig, horse; mouse; elephant). Exemplary MDM2 polypeptides are set forth in GenBank Accession no. Q9PVL2-1 for Gallus Gallus (Chicken), GenBank Accession no. NP_001092577.1 for Bos Taurus (Cattle), GenBank Accession no. W5PWI5-1 for Ovis Aries (sheep) and GenBank Accession no. NP_001098773.1 for Sus Scrofa (swine).

According to one embodiment, the cell derived vesicles contain additional peptides or polypeptides, such as tumor suppressors, immune modulators, MHC molecules, cytoskeletal proteins, membrane transport and fusion proteins, tetraspanins and/or proteins belonging to the heat-shock family, non-coding RNA molecules (e.g. miRNA, siRNAs, piRNAs, snoRNAs, snRNAs, exRNAs, scaRNAs, tRNAs, rRNAs and long ncRNAs).

Exemplary tumor suppressors include, but are not limited to, Retinoblastoma protein (pRb), maspin, pVHL, APC, CD95, STS, YPEL3, ST7, ST14, BRMS1, CRSP3, DRG1, KAI1, KISS1, NM23 and TIMPs.

Exemplary immune modulators include, but are not limited to, Hsp70 and galectin-5.

Exemplary miRNAs include, but are not limited to, miR-29b, miR-34b/c, miR-126, miR-150, miR-155, miR-181a/b, miR-375, miR-494, miR-495 and miR-551a.

According to one embodiment, the peptides, polypeptides (e.g. tumor suppressors or immune modulators) or non-coding RNA molecules are endogenous (e.g. originating from the cells releasing the cell derived vesicles).

According to another embodiment, the cell derived vesicles are genetically modified to further contain a peptide or polypeptide other than p53 (e.g. a tumor suppressor, an immune modulator, a non-coding RNA).

Accordingly, the exogenous genetic material (e.g. tumor suppressor, immune modulator, non-coding RNA genetic material) can be introduced into the cell derived vesicles by a various techniques. For example, the cell derived vesicles may be loaded by electroporation or the use of a transfection reagent. Despite the small size of cell derived vesicles (e.g. typically between 20-200 nm), previous publications have illustrated that it is possible to use electroporation and transfection reagent to load the cell derived vesicles with the exogenous genetic material including DNA and RNA (see for example European Patent No. EP2419144). Typical voltages are in the range of 20 V/cm to 1000 V/cm, such as 20V/cm to 100 V/cm with capacitance typically between 25 μF and 250 μF, such as between 25 μF and 125 μF. Alternatively, conventional transfection reagent can be used for transfection of cell derived vesicles with genetic material, such as but not limited to, cationic liposomes.

According to some embodiments of the invention, the cell derived vesicles are targeted to a desired cell or tissue (e.g. a cell comprising a mutant or a nonfunctional p53 protein). This targeting is achieved by expressing on the surface of the cell derived vesicles a heterologous moiety (also referred to as binding agent) which binds to a cell surface moiety expressed on the surface of the cell to be targeted. For example, the cell derived vesicles can be targeted to particular cell types or tissues by expressing on their surface a heterologous moiety such as a protein, a peptide or a glycolipid molecule. For example, suitable peptides are those which bind to cell surface moieties such as receptors or their ligands found on the cell surface of the cell to be targeted. Examples of suitable heterologous moieties are short peptides, scFv and complete proteins, so long as the binding agent can be expressed on the surface of the cell derived vesicle and does not interfere with expression of the active wild-type p53.

According to some embodiments of the invention, the cell derived vesicles are loaded with an additional therapeutic moiety such as a drug e.g., chemotherapy e.g. a cytotoxic moiety or a toxic moiety (e.g. such a small molecule).

Determination that the cell derived vesicles comprise specific components (e.g. wild-type active p53, phosphorylated p53, or additional tumor suppressors) can be carried out using any method known in the art, e.g. by Western blot, ELISA, FACS, MACS, RIA, Immunohistochemical analysis, In situ activity assay, and In vitro activity assays. Likewise, determination that the cell derived vesicles comprise a heterologous moiety (e.g. binding agent), a cytotoxic moiety or a toxic moiety, can be carried out using any method known in the art.

According to one embodiment, the cell derived vesicles are native cell derived vesicles, e.g. are obtained from natural cells or obtained from their natural environment (as discussed below).

According to one embodiment, the cell derived vesicles are not artificial cell derived vesicles (e.g. coated liposomes).

According to one embodiment, the cell derived vesicles are obtained from cells which express at least about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10% or more endogenous wild-type p53 protein of the total cellular proteins. Methods of measuring expression of p53 proteins in a cell are well known in the art and include, e.g. ELISA, Western blot analysis, and Flow cytometry assay (e.g. FACS).

According to a specific embodiment, the cell derived vesicles are obtained from cells which express at least 0.5% endogenous wild-type p53 protein of the total cellular proteins.

According to one embodiment of the invention, the cell derived vesicles are obtained from cells which naturally express p53.

According to one embodiment of the invention, the cell derived vesicles are obtained from cells which are not genetically manipulated to express p53 proteins or recombinant versions thereof (e.g. non-genetically modified cells).

According to one embodiment, the cell derived vesicles are obtained from cells which do not naturally express endogenous MDM2 polypeptide.

According to one embodiment, the cell derived vesicles are obtained from cells which express endogenous MDM2 polypeptide at a level not exceeding 0.01%, 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10% of the total cellular proteins. Methods of measuring expression of MDM2 polypeptides in a cell are well known in the art and include, e.g. ELISA, Western blot analysis, and Flow cytometry assay (e.g. FACS).

According to a specific embodiment, the cell derived vesicles are obtained from cells which express endogenous MDM2 polypeptide at a level not exceeding 0.5% of the total cellular proteins.

According to one embodiment, the cell derived vesicles are obtained from cells which have been treated with a MDM2 inhibitor. MDM2 inhibitors are well known in the art and include, for example, Nutlin-3, Spirooxindoles and 1,4-benzodiazepine-2,5-diones (BDP), as discussed in detail in Khoury and Domling, Curr Pharm Des. (2012) 18(30): 4668-4678, incorporated herein by reference.

According to one embodiment, cell derived vesicles (i.e. comprising an active wild-type p53) are obtained from healthy cells (e.g. non-cancerous cells).

According to one embodiment, cell derived vesicles (i.e. comprising an active wild-type p53) are obtained from genetically non-modified cells.

According to one embodiment, cell derived vesicles (i.e. comprising an active wild-type p53) are obtained from genetically modified cells. Accordingly, the cells may be genetically engineered to express additional peptides, polypeptides or heterologous moieties (e.g. binding agents e.g. for specific targeting of a target cell).

As cell derived vesicles are derived from a variety of different cells, cells (e.g. animal cells, as discussed below) may be genetically engineered with an exogenous genetic material (including DNA and RNA) for expression of a polypeptide of choice (e.g. a tumor suppressor or immune activator). These cells are then cultured for an ample amount of time to produce cell derived vesicles (e.g. for 1, 2, 3, 4, 5, 6, 12, 24, 48, 72, 96 hours, for several days e.g. 1, 2, 3, 4, 5, 6, 7, 8, 9, 10, 12, 14, 21 or 30 days, or for several weeks e.g. 1, 2, 3, 4, 5, 6, 7, 8, 10, 12 or 14 weeks) prior to harvesting of the cell derived vesicles.

According to one embodiment, cell derived vesicles (i.e. comprising an active wild-type p53) are obtained from animal cells.

According to one embodiment, cell derived vesicles (i.e. comprising an active wild-type p53) are obtained from cells of an animal selected from a fish, an amphibian, a reptile, a bird and a mammal.

According to one embodiment, the animal is a mammal, including but not limited to a mouse, a rat, a hamster, a guinea pig, a gerbil, a hamster, a rabbit, a cat, a dog, a pig (e.g. swine), a cow, a goat, a sheep, a primate, an elephant and a horse.

According to one embodiment, the animal is a bird, including but not limited to, a chicken, a turkey, a duck, and a swan.

According to one embodiment, cell derived vesicles comprising an active wild-type p53 are obtained from cells of various tissues including, but not limited to, eye tissues (e.g. corneal epithelium tissue, conjunctiva tissue), epidermis, testicles, epithelium of small intestines and a brain tissues (e.g. cerebellum, hippocampus, hypothalamus, pons, thalamus and upper cerebral spine).

According to a specific embodiment, cell derived vesicles comprising an active wild-type p53 are obtained from cells of an eye tissue (e.g., of human, pig or a chicken).

According to one embodiment, cell derived vesicles comprising an active wild-type p53 are obtained from various cell types, including but not limited to, eye cells (e.g. corneal epithelium cells, conjunctival cells), intestinal epithelial cells, skin epithelial cells, skin fibroblasts, brain hippocampus cells and other cell types. According to one embodiment, cell derived vesicles are obtained from eye cells.

Eye cells refer to any cell existing in an eye, including cells existing in eyelid, sclera and cornea.

Accordingly, cell derived vesicles comprising an active wild-type p53 may be obtained from any eye cells including but not limited to, cells of the sclera tissue, cells of the cornea tissue (e.g. epithelial cells, endothelial cells, etc.), cells of conjunctival tissue (e.g. melanocytes, T and B cell lymphocytes) and cells of the eyelid.

According to a specific embodiment, eye cells which release cell derived vesicles comprising an active wild-type p53 comprise corneal cells. In human, the cornea is stated to be composed of five layers from the external side (body surface) in order, and is composed of corneal epithelium, Bowman's membrane (external boundary line), Lamina propria, Descemet's membrane (internal boundary line), and corneal endothelium from the external side.

Exemplary corneal cells which release cell derived vesicles comprising an active wild-type p53, include but are not limited to, corneal epithelial cells.

According to a specific embodiment, eye cells which release cell derived vesicles comprising an active wild-type p53 comprise conjunctival cells. In human, conjunctiva comprises non-keratinized, stratified squamous epithelium with goblet cells, and also stratified columnar epithelium.

Exemplary conjunctival cells which release cell derived vesicles comprising an active wild-type p53, include but are not limited to, conjunctival epithelial cells.

Depending on the application, the cell derived vesicles comprising an active wild-type p53 may be obtained from cells of an organism which is syngeneic or non-syngeneic with a subject to be treated (discussed in detail hereinbelow).

As used herein, the term "syngeneic" cells refer to cells which are essentially genetically identical with the subject or essentially all lymphocytes of the subject. Examples of syngeneic cells include cells derived from the subject (also referred to in the art as an "autologous"), from a clone of the subject, or from an identical twin of the subject.

As used herein, the term "non-syngeneic" cells refer to cells which are not essentially genetically identical with the subject or essentially all lymphocytes of the subject, such as allogeneic cells or xenogeneic cells.

As used herein, the term "allogeneic" refers to cells which are derived from a donor who is of the same species as the subject, but which is substantially non-clonal with the subject. Typically, outbred, non-zygotic twin mammals of the same species are allogeneic with each other. It will be appreciated that an allogeneic cell may be HLA identical, partially HLA identical or HLA non-identical (i.e. displaying one or more disparate HLA determinant) with respect to the subject.

As used herein, the term "xenogeneic" refers to a cell which substantially expresses antigens of a different species relative to the species of a substantial proportion of the lymphocytes of the subject. Typically, outbred mammals of different species are xenogeneic with each other.

The present invention envisages that xenogeneic cells are derived from a variety of species. Thus, according to one embodiment, the cell derived vesicles may be obtained from cells of any animal (e.g. mammal). Suitable species origins for the cell derived vesicles (or cells releasing same) comprise the major domesticated or livestock animals and primates. Such animals include, but are not limited to, poultry (e.g. chicken), porcines (e.g. pig or swine), bovines (e.g., cow), equines (e.g., horse), ovines (e.g., goat, sheep), felines (e.g., *Felis Domestica*), canines (e.g., *Canis Domestica*), rodents (e.g., mouse, rat, rabbit, guinea pig, gerbil, hamster), primates (e.g., chimpanzee, rhesus monkey, macaque monkey, marmoset), and elephants.

Cell derived vesicles (or cells releasing same) of xenogeneic origin (e.g. porcine origin) are preferably obtained from a source which is known to be free of zoonoses, such as porcine endogenous retroviruses. Similarly, human-derived cell derived vesicles, cells or tissues are preferably obtained from substantially pathogen-free sources.

According to one embodiment, the cell derived vesicles (or cells releasing same) are non-syngeneic with the subject.

According to one embodiment, the cell derived vesicles of the invention are obtained from cells allogeneic with the subject.

According to one embodiment, the cell derived vesicles of the invention are obtained from cells xenogeneic with the subject.

According to one embodiment, the cell derived vesicles of the invention are obtained from cells syngeneic with the subject (e.g. autologous).

According to an embodiment of the present invention, the subject is a human being having a disease, disorder or condition associated with a mutant or a nonfunctional p53 protein, and the cell derived vesicles are obtained from cells from a human origin (e.g. syngeneic or non-syngeneic with the subject).

According to one embodiment, the subject is a human being having a disease, disorder or condition associated with a mutant or a nonfunctional p53 protein, and the cell derived vesicles of the invention are obtained from cells of a xenogeneic origin (e.g. chicken, cattle, swine or elephant).

Depending on the application and available sources, the cell derived vesicles of the invention are obtained from cells of a prenatal organism, postnatal organism, an adult or a cadaver. Such determinations are well within the ability of one of ordinary skill in the art.

As mentioned above, the proteinaceous preparation comprising cell derived vesicles according to the present invention is devoid of intact cells.

As used herein, the phrase "devoid of intact cells", when relating to the compositions of the present invention relates to a composition that is essentially without intact cells.

According to a specific embodiment, the composition comprises less than 1%, 2%, 3%, 4%, 5%, 10%, 15%, or 20% intact cells per ml fluid sample.

According to one embodiment, the composition of the present invention which is substantially free of intact cells comprises no more than 1 intact cell per about 100 cell derived vesicles, no more than 1 intact cell per about 1,000 cell derived vesicles, no more than 1 intact cell per about 10,000 cell derived vesicles, no more than 1 intact cell per about 100,000 cell derived vesicles, no more than 1 intact cell per about 1 million cell derived vesicles, no more than 1 intact cell per about 10 million cell derived vesicles, no more than 1 intact cell per about 100 million cell derived vesicles, no more than 1 intact cell per about 1 billion cell derived vesicles, no more than 1 intact cell per about 10 billion cell derived vesicles, or essentially does not comprise any intact cells.

Measuring the number of intact cells in a composition can be carried out using any method known in the art, such as by light microscopy or cell staining methods.

According to one embodiment, at least 10%, 20%, 30%, 40%, 50%, 60%, 70%, 80%, 90%, or 100% of the proteins in the proteinaceous preparation are in the cell derived vesicles.

According to a specific embodiment, at least 50% of the proteins in the proteinaceous preparation are in the cell derived vesicles.

According to one embodiment, there is provided a method of obtaining cell derived vesicles comprising active wild-type p53.

According to one embodiment, there is provided a method of obtaining cell derived vesicles comprising active wild-type p53, the method comprising isolating cell derived vesicles from a biological sample comprising cells, thereby obtaining cell derived vesicles comprising active p53.

According to one embodiment, obtaining cell derived vesicles from a biological sample is carried out without the use of a DNA damaging agent.

According to one embodiment, in order to increase secretion of cell derived vesicles from cells (e.g. cell secreted vesicles), the cells are treated with a DNA damaging agent (UV) as discussed below.

According to one embodiment, there is provided a method of obtaining cell derived vesicles comprising an active wild-type p53, the method comprising: (i) isolating cell derived vesicles from a biological sample; and (ii) treating the cell derived vesicles with a DNA damaging agent, thereby obtaining cell derived vesicles comprising active p53.

According to one embodiment, there is provided a method of obtaining cell derived vesicles comprising an active wild-type p53, the method comprising: (i) treating cells with a DNA damaging agent; and (ii) isolating cell derived vesicles from a biological sample comprising the cells, thereby obtaining cell derived vesicles comprising active p53.

The term "isolated" as used herein refers to at least partially separated from the natural environment e.g., from a body.

Cell derived vesicles can be isolated from any biological sample (e.g., fluid or hard tissue) comprising cell derived vesicles. Examples of fluid samples include, but are not limited to, whole blood, plasma, serum, spinal fluid, lymph fluid, bone marrow suspension, cerebrospinal fluid, brain fluid, ascites (e.g. malignant ascites), tears, saliva, sweat, urine, semen, sputum, ear flow, vaginal flow, secretions of the respiratory, intestinal and genitourinary tracts, milk, amniotic fluid, and samples of ex vivo cell culture constituents. Examples of tissue samples include, but are not limited to, surgical samples, biopsy samples, tissues, feces, and cultured cells. According to a specific embodiment, the tissue sample comprises a whole or partial organ (e.g. eye, brain, testicle, skin, intestine), such as those obtained from a cadaver or from a living subject undergoing whole or partial organ removal.

Methods of obtaining such biological samples are known in the art, and include without being limited to, standard blood retrieval procedures, standard urine and semen retrieval procedures, lumbar puncture, fine needle biopsy, needle biopsy, core needle biopsy and surgical biopsy (e.g., organ or brain biopsy), buccal smear and lavage. Regardless of the procedure employed, once a biopsy/sample is obtained cell derived vesicles can be obtained therefrom.

According to one embodiment, the biological sample comprises cell derived vesicles (or is further processed to comprise cell derived vesicles, such as cell secreted vesicles, as discussed below) and is essentially without intact cells.

According to a specific embodiment, the biological sample (e.g. processed sample) comprises less than 1%, 2%, 5%, 10%, 20%, 30%, 40%, 50%, 60%, 70%, 80% or 90% intact cells per ml fluid sample.

However, the biological sample may contain some cells or cell contents. The cells can be any cells which are derived from the subject (as discussed in detail above).

The volume of the biological sample used for obtaining cell derived vesicles can be in the range of between 0.1-1000 mL, such as about 1000, 750, 500, 250, 100, 75, 50, 25, 15, 10, 9, 8, 7, 6, 5, 4, 3, 2, 1 or 0.1 mL.

The biological sample of some embodiments of the invention may comprise cell derived vesicles in various ranges, e.g. 1, 5, 10, 15, 20, 25, 50, 100, 150, 200, 250, 500, 1000, 2000, 5000, 10,000, 50,000, 100,000, 500,000, $1 \times 10^6$ or more cell derived vesicles.

According to one embodiment, cell derived vesicles (e.g. cell secreted vesicles) are obtained from cell lines or primary cultures of cells expressing at least 0.5% endogenous wild-type p53 protein.

According to one embodiment, cell derived vesicles (e.g. cell secreted vesicles) are obtained from a freshly collected biological sample or from a biological sample that has been stored cryopreserved or cooled.

According to one embodiment, cell derived vesicles (e.g. cell secreted vesicles) are obtained from a culture medium in which the cells have been cultured.

For example, cell derived vesicles (e.g. cell secreted vesicles, including exosomes) can be isolated from the biological sample by any method known in the art. Suitable methods are taught, for example, in U.S. Pat. Nos. 9,347,087 and 8,278,059, incorporated herein by reference.

For example, cell derived vesicles (e.g. cell secreted vesicles, including exosomes) may be obtained from a fluid sample by first removing any debris from the sample e.g. by precipitation with a volume-excluding polymer (e.g. polyethylene glycol (PEG) or dextrans and derivatives such as dextran sulfate, dextran acetate, and hydrophilic polymers such as polyvinyl alcohol, polyvinyl acetate and polyvinyl sulfate). Methods of clarification include centrifugation, ultracentrifugation, filtration or ultrafiltration. The skilled artisan is aware of the fact, that an efficient separation might require several centrifugation steps using different centrifugation procedures, temperatures, speeds, durations, rotors, and the like. For example, suitable volume-excluding polymers may have a molecular weight between 1000 and 1,000,000 daltons. In general, when higher concentrations of cell derived vesicles (e.g. exosomes) are present in a sample, lower molecular weight polymers may be used. Volume-excluding polymers may be used at a final concentration of from 1% to 90% (w/v) upon mixing with the sample. A variety of buffers commonly used for biological samples may be used for incubation of the cell derived vesicles (e.g. exosome) sample with the volume-excluding polymer including phosphate, acetate, citrate and TRIS buffers. The pH of the buffer may be any pH that is compatible with the sample, but a typical range is from 6 to 8. Incubation of the biological sample with the volume-excluding polymer may be performed at various temperatures, e.g. 4° C. to room temperature (e.g. 20° C.). The time of incubation of the sample with the volume-excluding polymer may be any, typically in the range 1 minute to 24 hours (e.g. 30 minutes to 12 hours, 30 minutes to 6 hours, 30 minutes to 4 hours, or 30 minutes to 2 hours). One of skill in the art is aware that the incubation time is influenced by, among other factors, the concentration of the volume-excluding polymer, the molecular weight of the volume-excluding polymer, the temperature of incubation and the concentration of cell derived vesicles (e.g. exosomes) and other components in the sample. After completion of the incubation of the sample with the volume-excluding polymer the precipitated cell derived vesicles (e.g. exosomes) may be isolated by centrifugation, ultracentrifugation, filtration or ultrafiltration.

According to one embodiment, cell derived vesicles (e.g. exosomes) are separated from a biological fluid sample by first centrifugation of the biological sample (e.g. fluid sample such as plasma) at 1000×g for 15 minutes, then passing the sample through a filter (e.g. 0.1-0.5 μm filter, e.g. 0.2 μm filter) and centrifugation at about 100,000×g for 60-120 minutes (e.g. 90 minutes). Centrifugation can be repeated (e.g. after suspending the pellet in phosphate-buffered saline (PBS)) under the same conditions.

When isolating cell derived vesicles from tissue, cell line or primary culture sources it may be necessary to homogenize the tissue in order to obtain a homogenate containing cell derived vesicles. When isolating cell derived vesicles from tissue samples it is important to select a homogenization procedure that does not result in disruption of the cell derived vesicles.

According to one embodiment, cell derived vesicles are isolated from a tissue (e.g. eye tissue) by first harvesting the tissue (e.g. eye tissue) from a donor (e.g. animal) and homogenating the tissue as to obtain a homogenate. The entire tissue may be used, or alternatively a specific part of the tissue may be used. The cell derived vesicles are then isolated by centrifugation, ultracentrifugation, filtration or ultrafiltration.

According to one embodiment, the tissue is kept in ice prior to homogenization thereof. According to one embodiment, the cell line or primary culture is cultured in a culture medium prior to obtaining a cell derived vesicles therefrom. One of ordinary skill in the art is capable of determining the length of time of which the cells may be cultured. According to one embodiment, the cells are cultured for 12 hours, 24 hours, 36 hours, 48 hours, 3 days, 4 days, 5 days, 6 days, 7 days, 10 days, 14 days, 21 days, 30 days or more.

According to one embodiment, in order to stabilize and/or activate and/or prolong the half-life and/or increase the cellular levels of the p53 protein in a cell derived vesicles, the wild-type p53 is subjected to phosphorylation.

According to one embodiment, phosphorylation of p53 is performed by exposure to a DNA damaging agent.

As used herein, the term "DNA damaging agent" refers to any agent which causes damage either directly or indirectly to the nucleotides in the genome.

Exemplary DNA damaging agent include, but are not limited to, ultraviolet radiation (UV); ionizing radiation (IR) (e.g. gamma irradiation); chemotherapeutic agent; chemical compounds e.g. platinum-based compounds such as cisplatin; intercalating agents e.g. benzo[a]pyrenes, daunorubicin and actinomycin-D; DNA alkylating agents e.g. nitrogen mustards, methyl methanesulphonate (MMS), N-nitroso-N-methylurea (NMU) and N-ethyl-N-nitrosourea (ENU); psoralens; oxidative stress; hypoxia; and nutrient deprivation.

According to a specific embodiment, the DNA damaging agent is a UV irradiation.

According to one embodiment, the tissue is treated with a DNA damaging agent prior to homogenization thereof. According to one embodiment, this step is performed in a donor (e.g. animal) prior to harvesting of the tissue. Additionally or alternatively, a tissue is treated with a DNA damaging agent following harvesting thereof from a donor (e.g. animal).

According to one embodiment, the cells are treated with a DNA damaging agent prior to isolation of the cell derived vesicles. According to one embodiment, this step is performed in a tissue culture plate.

According to one embodiment, the isolated cell derived vesicles are treated with a DNA damaging agent.

According to another embodiment, any combination of a tissue, cells and/or the isolated cell derived vesicles are treated with a DNA damaging agent.

According to a specific embodiment, eye tissue is used for isolation of cell derived vesicles containing wild-type active p53. Accordingly, the eye (or part thereof) is harvested from a donor animal (e.g. animal) and is homogenated as to obtain cell derived vesicles. It will be appreciated that the entire eye tissue may be used, or alternatively, a specific tissue may be selected and harvested from the eye (e.g. cornea tissue or conjunctival tissue). The cell derived vesicles are isolated by centrifugation, ultracentrifugation, filtration or ultrafiltration.

According to one embodiment, the eye cells are treated with a DNA damaging agent prior to isolation of the cell derived vesicles. According to one embodiment, this step is performed in a tissue culture plate.

According to one embodiment, the cell derived vesicles are first isolated and are then treated with a DNA damaging agent.

The exosomal sample may be further purified or concentrated prior to use. For example, a heterogeneous population of cell derived vesicles can be quantitated (i.e. total level of cell derived vesicles in a sample), or a homogeneous population of cell derived vesicles, such as a population of cell derived vesicles with a particular size, with a particular marker profile, obtained from a particular type of biological sample (e.g. urine, serum, plasma, etc.) or derived from a particular cell type (e.g. eye cells, brain cells, skin cells, epithelial cells, intestinal cells) can be isolated from a heterogeneous population of cell derived vesicles and quantitated.

According to one embodiment, cell derived vesicles are selected for expression of activated (e.g. phosphorylated) wild-type p53 (e.g. phosphorylated). Any method known in the art for measuring expression of p53 protein or phosphorylated variant thereof can be used, such as but not limited to, ELISA, Western blot analysis, FACS, Immunohistochemical analysis, In situ activity assay and In vitro activity assays.

According to one embodiment, the contents of the cell derived vesicles may be extracted for characterization of cell derived vesicles containing activated wild-type 53.

According to one embodiment, cell derived vesicles are purified or concentrated from a biological sample using size exclusion chromatography, density gradient centrifugation, differential centrifugation, nanomembrane ultrafiltration, immunoabsorbent capture, affinity purification, microfluidic separation, or combinations thereof.

Size exclusion chromatography, such as gel permeation columns, centrifugation or density gradient centrifugation, and filtration methods can be used. For example, cell derived vesicles can be isolated by differential centrifugation, anion exchange and/or gel permeation chromatography (as described e.g. in U.S. Pat. Nos. 6,899,863 and 6,812,023), sucrose density gradients, organelle electrophoresis (as described e.g. in U.S. Pat. No. 7,198,923), magnetic activated cell sorting (MACS), or with a nanomembrane ultrafiltration concentrator. Thus, various combinations of isolation or concentration methods can be used as known to one of skill in the art.

Sub-populations of cell derived vesicles may be isolated using other properties of the cell derived vesicles such as the expression of other tumor suppressors, immune modulators, cytoskeletal proteins, membrane transport and fusion proteins, tetraspanins and/or proteins belonging to the heat-shock family (as discussed in detail hereinabove). Any method known in the art for measuring expression of a protein can be used, such as but not limited to, ELISA, Western blot analysis, FACS, Immunohistochemical analysis, In situ activity assay and In vitro activity assays. Furthermore, the contents of the cell derived vesicles may be extracted for characterization of cell derived vesicles containing any of the above mentioned polypeptides (as discussed in detail hereinabove).

Additionally or alternatively, sub-populations of cell derived vesicles may be isolated using other properties of the cell derived vesicles such as the presence of surface markers. Surface markers which may be used for fraction of cell derived vesicles include but are not limited to tumor markers, cell type specific markers and MHC class II markers. MHC class II markers which have been associated with cell derived vesicles include HLA DP, DQ and DR haplotypes. Other surface markers associated with cell derived vesicles include, but are not limited to, CD9, CD81, CD63, CD82, CD37, CD53, or Rab-5b (Thery et al. Nat. Rev. Immunol. 2 (2002) 569-579; Valadi et al. Nat. Cell. Biol. 9 (2007) 654-659).

As an example, cell derived vesicles having CD63 on their surface may be isolated using antibody coated magnetic particles e.g. using Dynabeads®, super-paramagnetic polystyrene beads which may be conjugated with anti-human CD63 antibody either directly to the bead surface or via a secondary linker (e.g. anti-mouse IgG). The beads may be between 1 and 4.5 µm in diameter. Accordingly, the antibody coated Dynabeads® may be added to a cell derived vesicle sample (e.g. prepared as described above) and incubated at e.g. 2-8° C. or at room temperature from 5 minutes to overnight. Dynabeads® with bound cell derived vesicles may then be collected using a magnet. The isolated, bead bound cell derived vesicles may then be resuspended in an appropriate buffer such as phosphate buffered saline and used for analysis (qRT-PCR, sequencing, western blot, ELISA, flow cytometry, etc. as discussed below). Similar protocols may be used for any other surface marker for which an antibody or other specific ligand is available. Indirect binding methods such as those using biotin-avidin may also be used.

Determining the level of cell derived vesicles (e.g. exosomes) in a sample can be performed using any method known in the art, e.g. by ELISA, using commercially available kits such as, for example, the ExoQuick kit (System Biosciences, Mountain View, Calif.), magnetic activated cell sorting (MACS) or by FACS using an antigen or antigens which bind general cell derived vesicles (e.g. exosome) markers, such as but not limited to, CD63, CD9, CD81, CD82, CD37, CD53, or Rab-5b.

According to one embodiment, once an isolated cell derived vesicles sample has been prepared it can be stored, such as in a sample bank or freezer (e.g. at −25° C.) and retrieved for therapeutic purposes as necessary, alternatively, the cell derived vesicles sample can be directly used without storing the sample.

According to one aspect of the present invention there is provided a method of treating a disease, disorder or condition associated with a mutant or a nonfunctional p53 protein in a subject in need thereof, the method comprising administering to the subject a therapeutically effective amount of the pharmaceutical composition of some embodiments of the invention.

According to one aspect of the present invention there is provided an effective amount of the pharmaceutical composition of some embodiments of the invention for use in treating a disease, disorder or condition associated with a mutant or a nonfunctional p53 protein in a subject in need thereof.

According to one aspect of the present invention there is provided a method of treating a disease, disorder or condition associated with a mutant or a nonfunctional p53 protein in a subject in need thereof, the method comprising administering to the subject a therapeutically effective amount of cell derived vesicles, the cell derived vesicles obtained from cells expressing at least 0.5% endogenous wild-type p53 protein of the total cellular proteins and not expressing recombinant p53 protein.

According to one aspect of the present invention there is provided a therapeutically effective amount of cell derived vesicles obtained from cells expressing at least 0.5% endogenous wild-type p53 protein of the total cellular proteins and not expressing recombinant p53 protein, for use in treating a disease, disorder or condition associated with a mutant or a nonfunctional p53 protein in a subject in need thereof.

The term "treating" refers to arresting the development of a pathology (disease, disorder or condition) and/or causing the reduction, remission, or regression of a pathology. Those of skill in the art will understand that various methodologies and assays can be used to assess the reduction, remission or regression of a pathology. It will be appreciated that the treating may be performed alone or in conjunction with other therapies.

As used herein, the terms "subject" or "subject in need thereof" include mammals, preferably human beings at any age or gender. The subject may be showing preliminary signs of a pathology, e.g. a disease, disorder or condition associated with a mutant or a nonfunctional p53 protein, e.g., hyperproliferative disease.

The phrase "a disease, disorder or condition associated with a mutant or a nonfunctional p53 protein" refers to a condition which is caused (at least in part) by, or is related to, the presence of nonfunctional or mutated p53 protein in a cell, a tissue, an organ, or a body.

It will be appreciated that since p53 is expressed from both alleles, the overall content of intracellular p53 in a cell can be either wild-type (wt/wt), mixture of wt and mutant p53 (wt/mut) or mutant p53 only (when both alleles are mutated (mut/mut), or one allele is deleted (mut/−)). In diseases, disorders or conditions associated with a mutant or a nonfunctional p53 protein, e.g. cancer, the situation is typically wt/mut, mut/mut or mut/−. However, since p53 acts as a tetramer, mutant or nonfunctional p53 proteins may abrogate the activity of wild-type p53 proteins, which do exist in the diseased cells.

According to one embodiment, the disease, disorder or condition associated with a mutant or a nonfunctional p53 protein is an Alzheimer's disease, a Parkinson's disease, a stroke, an Amyotrophic lateral sclerosis (ALS), a spinal cord injury, a Li-Fraumeni syndrome (also referred to as sarcoma, breast, leukemia and adrenal gland (SBLA) syndrome), an acute ischemic disease, multiple sclerosis and arthritis. Additional diseases are discussed in Gudkov and Komarova, *Cold Spring Harb Perspect Biol* (2010): 2:a001180, incorporated herein by reference.

According to one embodiment, the disease, disorder or condition associated with a mutant or a nonfunctional p53 protein is a hyperproliferative disease.

Examples of hyperproliferative disorders include, but are not limited to, diabetic retinopathy, psoriasis, endometriosis, macular degenerative disorders and benign growth disorders such as prostate enlargement and lipomas and keloids.

According to one embodiment, the disease, disorder or condition associated with a mutant or a nonfunctional p53 protein is a cancer.

As used herein the term "cancer" refers to any cancerous disease. Cancer cells may be associated with phenotypes such uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor, such cells may exist locally within an animal (e.g. solid tumor), alternatively, cancer cells may circulate in the blood stream as independent cells, for example, leukemic cells (non-solid tumor), or may be dispersed throughout the body (e.g.

metastasis). It will be appreciated that the term cancer as used herein encompasses all types of cancers, at any stage and in any form.

Types of cancerous diseases amenable to treatment by the methods of some embodiments of the invention include benign tumors, warts, polyps, pre-cancers, and malignant tumors/cancers.

According to one embodiment, the cancer is a solid tumor.
According to one embodiment, the cancer is a cancer metastasis.
According to one embodiment, the cancer is associated with a mutant or a nonfunctional p53 protein such that tumor suppression is compromised. According to one embodiment, the cancer is associated with an inherited germline TP53 mutation. According to one embodiment, the cancer is associated with a somatic TP53 mutation. According to one embodiment, the cancer associated with a mutant or non-functional p53 protein is selected from, but not limited to, breast cancer, bone and soft tissue sarcoma, brain tumor, adrenocortical carcinomas (ADC), leukemia, stomach cancer and colorectal cancer.

According to one embodiment, the cancer is a non-solid tumor such as a hematologic malignancy.

According to one embodiment, the non-solid tumor or hematologic malignancy is a leukemia or lymphoma.

Specific examples of cancerous diseases which can be treated using the methods of the present invention include, but are not limited to, tumors of the gastrointestinal tract (colon carcinoma, rectal carcinoma, colorectal carcinoma, colorectal cancer, colorectal adenoma, hereditary nonpolyposis type 1, hereditary nonpolyposis type 2, hereditary nonpolyposis type 3, hereditary nonpolyposis type 6; colorectal cancer, hereditary nonpolyposis type 7, small and/or large bowel carcinoma, esophageal carcinoma, tylosis with esophageal cancer, stomach carcinoma, pancreatic carcinoma, pancreatic endocrine tumors), endometrial carcinoma, dermatofibrosarcoma protuberans, gallbladder carcinoma, Biliary tract tumors, prostate cancer, prostate adenocarcinoma, renal cancer (e.g., Wilms' tumor type 2 or type 1), liver cancer (e.g., hepatoblastoma, hepatocellular carcinoma, hepatocellular cancer), anal cancer, penile cancer, bladder cancer, embryonal rhabdomyosarcoma, germ cell tumor, trophoblastic tumor, testicular germ cells tumor, immature teratoma of ovary, uterine, epithelial ovarian, sacrococcygeal tumor, choriocarcinoma, placental site trophoblastic tumor, epithelial adult tumor, ovarian carcinoma, serous ovarian cancer, ovarian sex cord tumors, cervical carcinoma, vaginal cancer, vulvar cancer, uterine cervix carcinoma, small-cell and non-small cell lung carcinoma, nasopharyngeal, breast carcinoma (e.g., ductal breast cancer, invasive intraductal breast cancer, sporadic; breast cancer, susceptibility to breast cancer, type 4 breast cancer, breast cancer-1, breast cancer-3; breast-ovarian cancer), squamous cell carcinoma (e.g., in head and neck), neurogenic tumor, astrocytoma, ganglioblastoma, neuroblastoma, lymphomas (e.g., Hodgkin's disease, non-Hodgkin's lymphoma, B cell, Burkitt, cutaneous T cell, histiocytic, lymphoblastic, T cell, thymic), gliomas, adenocarcinoma, adrenal tumor, hereditary adrenocortical carcinoma, brain malignancy (tumor), various other carcinomas (e.g., bronchogenic large cell, ductal, Ehrlich-Lettre ascites, epidermoid, large cell, Lewis lung, medullary, mucoepidermoid, oat cell, small cell, spindle cell, spinocellular, transitional cell, undifferentiated, carcinosarcoma, choriocarcinoma, cystadenocarcinoma), ependimoblastoma, epithelioma, erythroleukemia (e.g., Friend, lymphoblast), fibrosarcoma, giant cell tumor, glial tumor, glioblastoma (e.g., multiforme, astrocytoma), glioma hepatoma, heterohybridoma, heteromyeloma, histiocytoma, hybridoma (e.g., B cell), hypernephroma, insulinoma, islet tumor, keratoma, leiomyoblastoma, leiomyosarcoma, leukemia (e.g., acute lymphatic, acute lymphoblastic, acute lymphoblastic pre-B cell, acute lymphoblastic T cell leukemia, acute-megakaryoblastic, monocytic, acute myelogenous, acute myeloid, acute myeloid with eosinophilia, B cell, basophilic, chronic myeloid, chronic, B cell, eosinophilic, Friend, granulocytic or myelocytic, hairy cell, lymphocytic, megakaryoblastic, monocytic, monocytic-macrophage, myeloblastic, myeloid, myelomonocytic, plasma cell, pre-B cell, promyelocytic, subacute, T cell, lymphoid neoplasm, predisposition to myeloid malignancy, acute nonlymphocytic leukemia), lymphosarcoma, melanoma, mammary tumor, mastocytoma, medulloblastoma, mesothelioma, metastatic tumor, monocyte tumor, multiple myeloma, myelodysplastic syndrome, myeloma, nephroblastoma, nervous tissue glial tumor, nervous tissue neuronal tumor, neurinoma, neuroblastoma, oligodendroglioma, osteochondroma, osteomyeloma, osteosarcoma (e.g., Ewing's), papilloma, transitional cell, pheochromocytoma, pituitary tumor (invasive), plasmacytoma, retinoblastoma, rhabdomyosarcoma, sarcoma (e.g., Ewing's, histiocytic cell, Jensen, osteogenic, reticulum cell), schwannoma, subcutaneous tumor, teratocarcinoma (e.g., pluripotent), teratoma, testicular tumor, thymoma and trichoepithelioma, gastric cancer, fibrosarcoma, glioblastoma multiforme; multiple glomus tumors, Li-Fraumeni syndrome, liposarcoma, lynch cancer family syndrome II, male germ cell tumor, mast cell leukemia, medullary thyroid, multiple meningioma, endocrine neoplasia myxosarcoma, paraganglioma, familial nonchromaffin, pilomatricoma, papillary, familial and sporadic, rhabdoid predisposition syndrome, familial, rhabdoid tumors, soft tissue sarcoma, and Turcot syndrome with glioblastoma.

Precancers are well characterized and known in the art (refer, for example, to Berman J J. and Henson D E., 2003. Classifying the precancers: a metadata approach. BMC Med Inform Decis Mak. 3:8). Classes of precancers amenable to treatment via the method of the invention include acquired small or microscopic precancers, acquired large lesions with nuclear atypia, precursor lesions occurring with inherited hyperplastic syndromes that progress to cancer, and acquired diffuse hyperplasias and diffuse metaplasias. Examples of small or microscopic precancers include HGSIL (High grade squamous intraepithelial lesion of uterine cervix), AIN (anal intraepithelial neoplasia), dysplasia of vocal cord, aberrant crypts (of colon), PIN (prostatic intraepithelial neoplasia). Examples of acquired large lesions with nuclear atypia include tubular adenoma, AILD (angioimmunoblastic lymphadenopathy with dysproteinemia), atypical meningioma, gastric polyp, large plaque parapsoriasis, myelodysplasia, papillary transitional cell carcinoma in-situ, refractory anemia with excess blasts, and Schneiderian papilloma. Examples of precursor lesions occurring with inherited hyperplastic syndromes that progress to cancer include atypical mole syndrome, C cell adenomatosis and MEA. Examples of acquired diffuse hyperplasias and diffuse metaplasias include AIDS, atypical lymphoid hyperplasia, Paget's disease of bone, post-transplant lymphoproliferative disease and ulcerative colitis.

According to a specific embodiment, the solid tumor or metastasis is selected from the group consisting of an ovarian cancer, a cervical cancer, a vaginal cancer, a vulvar cancer, an anal cancer, a penile cancer, a breast cancer, an endometrial cancer, a head and neck cancer, a colon cancer, a colorectal cancer, a prostate cancer, a lung cancer, a melanoma, a lymphoma, a pancreatic cancer, a liver cancer and a splenic cancer.

According to a specific embodiment, the cancer is in a terminal stage.

According to a specific embodiment, the cancer is a terminal stage of chronic leukemia.

According to one embodiment, a sample of the subject is obtained prior to administering the cell derived vesicles (i.e. comprising an active wild-type p53) to assess that the disease, disorder or condition involves a mutant or a non-functional p53 protein.

As used herein "a sample" refers to a biological sample (e.g., fluid or hard tissue) which comprises the diseased cells (i.e. comprising mutant or a nonfunctional p53 protein). Examples of fluid samples include, but are not limited to, whole blood, plasma, serum, spinal fluid, lymph fluid, bone marrow suspension, cerebrospinal fluid, brain fluid, ascites (e.g. malignant ascites), tears, saliva, sweat, urine, semen, sputum, ear flow, vaginal flow, secretions of the respiratory, intestinal and genitourinary tracts, milk, amniotic fluid, and samples of in vivo cell culture constituents. Examples of tissue samples include, but are not limited to, surgical samples, biopsy samples, tissues, feces, and cultured cells.

Methods of obtaining such samples are known in the art, and include without being limited to, standard blood retrieval procedures, standard urine and semen retrieval procedures, lumbar puncture, fine needle biopsy, needle biopsy, core needle biopsy and surgical biopsy (e.g., organ or brain biopsy), buccal smear and lavage. Regardless of the procedure employed, once a biopsy/sample is obtained the level of the variant (i.e. mutant or a nonfunctional p53 protein) can be determined and a diagnosis can thus be made.

Assessing the presence of a mutant or a nonfunctional p53 protein can be carried out using any method known in the art, such as but not limited to, HPLC mutation screening assay, PCR and RT-PCR. Additional assays are discussed in Liu and Bodmer, PNAS (2006) 103(4): 976-981, incorporated herein by reference.

A sample of the subject is determined as having a disease, disorder or condition involving a mutant or a nonfunctional p53 protein when at least one mutation is found in a p53 protein in the sample.

According to one embodiment, a sample of the subject is determined as having a disease, disorder or condition involving a mutant or a nonfunctional p53 protein when at least about 0.001%, 0.005%, 0.01%, 0.05%, 0.1%, 0.5%, 1%, 2%, 5%, 10%, 25%, 50%, 60%, 70%, 80%, 90%, 99%, 100% or more of the cells in the sample express a mutant or a nonfunctional p53 protein.

According to one embodiment, a sample of the subject is determined as having a disease, disorder or condition involving a mutant or a nonfunctional p53 protein when at least one cell (e.g. 1, 2, 3, 4, 5, 10, 20, 50, 100, 1000 cells or more) in the sample expresses a mutant or a nonfunctional p53 protein. The cell derived vesicles comprising an active wild-type p53 of some embodiments can be used for inducing apoptosis of a target cell comprising a mutant or a nonfunctional p53 protein, the method comprising contacting the target cell with an effective amount of cell derived vesicles, the cell derived vesicles obtained from cells expressing at least 0.5% endogenous wild-type p53 protein of the total cellular proteins and not expressing recombinant p53 protein.

The term "target cell" refers to any cell which expresses a mutant or a nonfunctional p53 protein. Exemplary cells include, but are not limited to, cancer cells such as those of a solid tumor or metastasis or of a hematologic malignancy.

The term "apoptosis" as used herein refers to the cell process of programmed cell death. Apoptosis characterized by distinct morphologic alterations in the cytoplasm and nucleus, chromatin cleavage at regularly spaced sites, and endonucleolytic cleavage of genomic DNA at internucleosomal sites. These changes include blebbing, cell shrinkage, nuclear fragmentation, chromatin condensation, and chromosomal DNA fragmentation. Furthermore, apoptosis produces cell fragments called apoptotic bodies that phagocytic cells are able to engulf and quickly remove before the contents of the cell can spill out onto surrounding cells and cause damage.

According to one embodiment, the method of contacting the cell derived vesicles comprising an active wild-type p53 of the present invention with the targeted cell is effected in-vivo. According to one embodiment, the method of contacting the cell derived vesicles comprising an active wild-type p53 of the present invention with the targeted cell is effected ex-vivo. Ex vivo treatments are well known in the art and include, without being limited to, apheresis and leukapheresis.

According to an embodiment of the present invention, an effective amount of the cell derived vesicles comprising an active wild-type p53 of the present invention, is an amount selected to replace mutant or nonfunctional p53 by its normal, active p53 wild-type protein.

According to an embodiment of the present invention, an effective amount of the cell derived vesicles comprising an active wild-type p53 of the present invention, is an amount selected to promote tumor regression.

According to an embodiment of the present invention, an effective amount of the cell derived vesicles comprising an active wild-type p53 of the present invention, is an amount selected to initiate or restore apoptosis (i.e. cell apoptosis) of a target cell (i.e. diseased cell such as a cancer cell).

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays (see e.g. Examples 1-2 in the Examples section which follows). Furthermore, a dose can be formulated in animal models to achieve a desired concentration or titer (see e.g. Examples 3-4 in the Examples section which follows). Such information can be used to more accurately determine useful doses in humans.

The cell derived vesicles comprising an active wild-type p53 or compositions comprising same, of some embodiments of the invention, can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the cell derived vesicles comprising an active wild-type p53 accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

According to one embodiment, administering comprises a route selected from the group consisting of intravenous, intra-arterial, intratumoral, subcutaneous, intramuscular, transdermal and intraperitoneal.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

The term "tissue" refers to part of an organism consisting of cells designed to perform a function or functions. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol.

The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (e.g. cell derived vesicles comprising an active wild-type p53) effective to alleviate or ameliorate symptoms of a disorder (e.g., associated with a mutated or nonfunctional p53 protein) or prolong the survival of the subject being treated. Determination of a therapeutically effective amount is well within the capability of those skilled in the art, especially in light of the detailed disclosure provided herein, as discussed in detail above.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide the active ingredient at a sufficient amount to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The cell derived vesicles comprising an active wild-type p53 of the invention can be suitably formulated as pharmaceutical compositions which can be suitably packaged as an article of manufacture. Such an article of manufacture comprises a label for use in treating a disease, disorder or condition associated with a mutant or a nonfunctional p53 protein, the packaging material packaging a pharmaceutically effective amount of the cell derived vesicles comprising an active wild-type p53.

It will be appreciated that the cell derived vesicles comprising an active wild-type p53 or compositions comprising same of the present invention may be administered in combination with other known treatments, including but not limited to, pro-apoptotic agents, chemotherapeutic agents (i.e., a cytotoxic drug), hormonal therapeutic agents, radiotherapeutic agents, anti-proliferative agents and/or any other compound with the ability to reduce or abrogate the uncontrolled growth of aberrant cells comprising a mutant or nonfunctional p53 protein, such as hyperproliferative cells.

Exemplary pro-apoptotic agents (i.e. apoptosis inducers) which may be used in accordance with the present invention include those which affect cellular apoptosis through a variety of mechanisms, including DNA cross-linking, inhibition of anti-apoptotic proteins and activation of caspases. Exemplary pro-apoptotic agents include, but are not limited to, Actinomycin D, Apicidin, Apoptosis Activator 2, AT 101, BAM 7, Bendamustine hydrochloride, Betulinic acid, C 75, Carboplatin, CHM 1, Cisplatin, Curcumin, Cyclophosphamide, 2,3-DCPE hydrochloride, Deguelin, Doxorubicin hydrochloride, Fludarabine, Gambogic acid, Kaempferol, 2-Methoxyestradiol, Mitomycin C, Narciclasine, Oncrasin 1, Oxaliplatin, Piperlongumine, Plumbagin, Streptozocin, Temozolomide and TW 37, and combinations thereof.

Non-limiting examples of chemotherapeutic agents include, but are not limited to, platinum-based drugs (e.g., oxaliplatin, cisplatin, carboplatin, spiroplatin, iproplatin, satraplatin, etc.), alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, 6-mercaptopurine, methotrexate, leucovorin, capecitabine, cytarabine, floxuridine, fludarabine, gemcitabine (Gemzar®), pemetrexed (ALIMTA®), raltitrexed, etc.), plant alkaloids (e.g., vincristine, vinblastine, vinorelbine, vindesine, podophyllotoxin, paclitaxel (Taxol®), docetaxel (Taxotere®), etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), pharmaceutically acceptable salts thereof, stereoisomers thereof, derivatives thereof, analogs thereof, and combinations thereof.

Examples of hormonal therapeutic agents include, but are not limited to, aromatase inhibitors (e.g., aminoglutethimide, anastrozole (Arimidex®), letrozole (Femora®), vorozole, exemestane (Aromasin®), 4-androstene-3,6,17-trione (6-OXO), 1,4,6-androstatrien-3,17-dione (ATD), formestane (Lentaron®), etc.), selective estrogen receptor modulators (e.g., bazedoxifene, clomifene, fulvestrant, lasofoxifene, raloxifene, tamoxifen, toremifene, etc.), steroids (e.g., dexamethasone), finasteride, and gonadotropin-releasing hormone agonists (GnRH) such as goserelin, pharmaceutically acceptable salts thereof, stereoisomers thereof, derivatives thereof, analogs thereof, and combinations thereof.

Examples of radiotherapeutic agents include, but are not limited to, radionuclides such as .sup.47Sc, .sup.64Cu, .sup.67Cu, .sup.89Sr, .sup.86Y, .sup.87Y, .sup.90Y, .sup.105Rh, .sup.111Ag, .sup.111In, .sup.117mSn, .sup.149Pm, .sup.153Sm, 166Ho, .sup.177Lu, .sup.186Re, .sup.188Re, .sup.211At, and .sup.212Bi, optionally conjugated to antibodies directed against tumor antigens.

Exemplary anti-proliferative agents include, but are not limited to, mTOR inhibitors such as sirolimus (rapamycin), temsirolimus (CCI-779), and everolimus (RAD001); Akt inhibitors such as IL6-hydroxymethyl-chiro-inositol-2-(R)-2-O-methyl-3-O-octadecyl-sn-glycer ocarbonate, 9-methoxy-2-methylellipticinium acetate, 1,3 -dihydro-1-)1-((1-((4-(6-phenyl-1H-imidazo[4,5-g]quinoxalin-7-yl)phenyl) me-thyl)-4-piperidinyl)-2H-benzimidazol-2-one,10-(4'-(N-diethylamino)butyl)-2-chlorophenoxazine, 3-formylchromone thiosemicarbazone (Cu(II)Cl.sub.2 complex), API-2, a 15-mer peptide derived from amino acids 10-24 of the proto-oncogene TCL1 (Hiromura et al., J. Biol. Chem., 279:53407-53418 (2004), KP372-1, and the compounds described in Kozikowski et al., J. Am. Chem. Soc., 125:1144-1145 (2003) and Kau et al., Cancer Cell, 4:463-476 (2003); and combinations thereof.

The cell derived vesicles comprising an active wild-type p53 or compositions comprising same of the present invention may be administered prior to, concomitantly with or following administration of the latter.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat.

Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Procedures

Cell Lines

The tumor cell line HT-29 (i.e. human colorectal adenocarcinoma cells ATCC HTB-38) was used in these studies. HT-29 cells were cultured in 50 ml tissue culture flasks in 5 ml McCoy 5A medium at 37° C. After initial expansion, HT-29 cells were placed into 24 well plates. Seeding density was 200,000 cells in 1 ml of media per well.

Each cell line panel (described in Table 1, herein below) is grown using the ATCC recommended culture conditions. The indicated p53 wild-type, p53 mutant and null p53 cells are cultured in ATCC recommended media.

Active Agent

Eyes of male Sprague Dawley (SD) rats were harvested from already sacrificed animals. Cornea was dissected from eye tissue, incubated in culture medium and UV irradiated. Corneal epithelium was dissected from cornea and homogenated (as described below). Alternatively, cell derived vesicles were first harvested from corneal homogenates and were then subjected to UV irradiation inducing p53 phosphorylation (in the cell derived vesicles).

Chicken eyes were obtained from sacrificed animals. Eyes were kept in ice until use. Chicken eye tissue was obtained and corneal epithelia were used as a source for corneal homogenates to obtain native cell derived vesicles containing p53 (as described below). Chicken cornea was induced by UV irradiation, homogenate and cell derived vesicles were harvested (as described below). Alternatively, cell derived vesicles were first harvested from corneal homogenates and were then subjected to UV irradiation inducing p53 phosphorylation in the cell derived vesicles.

Similarly, swine eyes are obtained from sacrificed animals. Eyes are kept in ice until use. Swine eye tissue is obtained and corneal epithelia is used as a source for corneal homogenates to obtain native cell derived vesicles containing p53 (as described below). Swine cornea is induced by UV irradiation, homogenate and cell derived vesicles are harvested (as described below). Alternatively, cell derived vesicles are first harvested from corneal homogenates and are then subjected to UV irradiation inducing p53 phosphorylation in the cell derived vesicles.

Alternatively, culture medium and corneal homogenate is obtained from available human corneal epithelial cell lines (e.g. HCE from Episkin). P53 phosphorylation is induced by UV irradiation of cell lines. Following irradiation, cell derived vesicles are harvested.

Furthermore, other tissues including, skin (epidermis), testis (gonads), brain structures, and the epithelium of the small intestine are used as a source for native cell derived vesicles containing p53. Cell derived vesicles are obtained from these tissues in the same manner as for eye tissue.

For example, UV irradiation is carried out by irradiation with a UV lamp (312 nm) at 150 mJ/cm2. The tissue or cells (e.g. in a petri dish) is placed 15-30 cm above a UV light source (e.g. 4×6 W, 312 nm tube, power 50 W, TFP-10M, Vilber Lourmant, Torcy, France) for 5-15 minutes. The UV dosimetry is performed using a UV light meter (YK-34UV; Lutron Electronic, Taiwan).

EXO_001 and EXO_002 agents were obtained from rat and chicken cornea, respectively, as follows:

Isolation of Cell Derived Vesicles

Isolation of cell derived vesicles was performed from both tissue/cell homogenate and from culture medium after cell cultivation.

Homogenate Preparation and Isolation of Cell Derived Vesicles from Tissues/Cells Ultracentrifugation Method Tissues\cells were added to a Teflon grinder and homogenized in minimal needed volume of culture medium. Initial centrifugation (e.g., 10,000×g for 10 min) was used which separates cells and cell detritus from supernatants. After centrifugation, the pellets were discarded and the supernatants (optional) were passed through a filter 0.2 μm. The supernatants were collected and loaded on top of a 40% sucrose solution and second centrifugation was carried out (e.g., at 100,000×g for 1 hour). Due to their density, cell derived vesicles (e.g. exosomes) enter the sucrose solution. The sucrose solution was harvested, diluted with PBS or culture medium and centrifuged again (e.g., at 100,000×g for 1 hour) to pellet the cell derived vesicles (e.g. exosomes). The resultant exosomal pellets were re-suspended in McCoy 5A culture medium.

Precipitation Method—ExoQuick™

This method is carried out according to the manufacturer's instructions (System Biosciences). Briefly, culture medium of corneal epithelium cells lines or corneal epithelium cell homogenate was diluted in PBS and mixed with of ExoQuick-TC™ solution by inverting the tube several times. The sample was incubated at 4° C. then centrifuged twice (e.g., at 1,500×g for 30 and 5 minutes, respectively), in order to remove the supernatant. The supernatant was discarded, and the pellet was re-suspended in PBS.

Freezing Procedure of Cell Derived Vesicles

Cell derived vesicles (also referred to herein a microparticles) obtained from chicken or rat cornea, as described above, were stored frozen for about one year at −25° C. Prior to use, the cell derived vesicles were thawed in 1.5 ml eppendorf tubes for about 1 hour at 4° C.

Co-Culture of Cell Derived Vesicles and Malignant Cell Line

Two groups of cells were maintained in 4 well formats as follows:

Group 1: HT-29 cells were maintained as per manufacturer's instruction in ATCC-formulated McCoy 5A medium. Fetal bovine serum added to medium to a final concentration of 10%. The HT-29 cells were not treated.

Group 2: HT-29 cells were treated with the active agent prepared as described in the 'materials and experimental procedures section' above, and applied to the tumor line in 1 ml of cell culture media for 24 hours.

Three days after treatment, the cells were fixed and stained for apoptosis.

Apoptosis Assay

Apoptosis was determined using an Apoptosis Kit (Annexin V-FITC Kit) for sensitive detection of early-stage apoptosis (MEBCYTO) MBL, following the manufacturer's described procedure.

Cell Morphology

Cell morphology was observed under Nikon™ microscopy, and images of the indicated cell lines were captured by Olympus® digital camera.

Cell Proliferation

Cell growth kinetics is monitored for 10 days by CellTiter 96® AQueous One Solution Cell Proliferation Assay (Promega).

Cell Apoptosis

HT-29 cells were seeded at a density of 200,000 cells in 1 ml of media per well in transwell-24. Twenty four hours after seeding, cells were treated with 100 µl of native cell derived vesicles. Twenty four hours later, apoptosis was determined using an Apoptotic Kit (Annexin V-FITC Kit) for detection of early-stage apoptosis (MEBCYTO) MBL.

Apoptotic Index Determination:

The apoptotic index (AI) was calculated as the percentage of apoptotic-positive stained with anti-Annexin V-FITC cells per 1,000 cells treated with the native cell derived vesicles.

Example 1

Anti-Cancer Effect of the Native Cell Derived Vesicles on Malignant Cells

Corneal epithelium is one of the most cancer resistant tissue types. Based on previous research [Tendler Y et al., (1999) supra; Pokroy R. et al., (2002) supra; Tendler Y et al. (2006) supra; Tendler Y et al., (2013) supra], this resistance was associated with high levels of p53 in the cytoplasm of corneal epithelial cells (FIGS. 1A-B) and absence of MDM2 (i.e. which inactivates p53) (FIGS. 2A-B). Furthermore, based on previous research [Tendler Y et al. (2015) Abstract 463, supra], MDM2-60 cleavage product was found in various normal ocular tissues: the lens, iris and retina; while in the normal corneal epithelium and conjunctiva MDM2 protein was absent (FIGS. 2A-B). Since MDM2 is the major E3 ubiquitin ligase of p53, its absence can be the reason for ineffective ubiquitination and accumulation of p53 protein in corneal epithelium. In agreement with the above results, Adachi [Adachi et al., Invest Ophthalmol Vis Sci. (2006) 47(9): 3801-10] also experimentally showed complete absence of MDM2 protein in corneal epithelium.

p53 containing exosomes were previously discovered [Tendler Y et al. (2015) Abstract 463, supra]. Significant amount of these exosomes were found using electronic microscope in corneal mucin layer of mice and humans (FIGS. 3A-B). Cellular compartments known as multivesicular endosomes and exosomes containing p53 protein were found in corneal epithelium cells (FIG. 4).

In the case of UV-irradiation, such cytoplasmic p53 can play an essential role in the prevention of corneal and conjunctival cancer. This is confirmed by the fact that homozygous p53 knockout mice developed ocular tumors after UV irradiation [Ananthaswamy HN, et al. Oncogene (1999) 18, 4247-53].

In view of the above, the present inventors tested the feasibility of treating human cancer cells by native cell derived vesicles (of animal origin) containing the p53 protein (see FIGS. 3A-B).

As illustrated in FIGS. 5A-C, untreated HT-29 cells (Group 1) maintained their tumor phenotype by visual inspection and discoloration of media (FIG. 5A, left panel). In sharp contrast, after 3 days of culture in the presence of native cell derived vesicles containing the p53 protein, the cell media comprising HT-29 cells (Group 2) was not discolored (FIG. 5A, right panel). Moreover, lower numbers of HT-29 cells in Group 2 (about 25-30% less) were evident as compared to the HT-29 cells of the control (Group 1) (FIGS. 5B-C). Furthermore, apoptosis in group 2 was significantly higher compared to the control group (FIGS. 6A and 6B).

This example illustrates that cell derived vesicles obtained from normal corneal epithelial cells have beneficial effects in the therapy of neoplasia in vitro.

The same experiment was conducted with the rat corneal epithelium replaced by chicken or swine corneal epithelia, and comparable results were obtained (FIGS. 11A-B). In addition, other tissues including skin, testis, brain, and the epithelium of the small intestine were used as a source of native cell derived vesicles containing p53, and comparable results were obtained (data not shown).

Example 2

Anti-Cancer In Vitro Studies

The present inventors are testing growth retardation and/or apoptotic effect of concentrated p53 containing cell derived vesicles on malignant cell lines. The cell line panels used (depicted in detail in Table 1, below) all contain mutant p53 and originate from solid and hematologic tumors.

TABLE 1

| ATCC cell line panels | | |
|---|---|---|
| | Cell line type | ATCC Number |
| p53 Hotspot Mutation Cell Panels | Breast Cancer | TCP-2010 ™ |
| | Colon Cancer | TCP-2020 ™ |
| | Non-Small Cell Lung Cancer | TCP-2030 ™ |
| | Small Cell Lung Cancer | TCP-2040 ™ |
| | Lymphoma | TCP-2050 ™ |
| | Pancreatic Cancer | TCP-2060 ™ |
| | Leukemia | TCP-2070 ™ |
| Human papilloma virus cell lines | Cervical Cancer - mutant p53 | HTB-35 ™ |
| | Cervical dysplasia - WT p53 | VRMC-29 ™ |
| | Bone Marrow/Stroma - WT p53 | CRL-2496 ™ |

The cells line panels used include, for example, the Lymphoma p53 Hotspot Mutation Cell Panel (ATCC® No. TCP-2050™) is composed of five selected suspension cell lines derived from lymphomas. This panel combines wild-type p53 cell lines with mutant p53 cell lines that carry hotspot mutations in one of the following codons: 248 and 273.

Another cell line panel used, includes for example, the Leukemia p53 Hotspot Mutation Cell Panel (ATCC® No.

TCP-2070™) is composed of six select suspension cell lines derived from individuals with leukemia. This panel combines wild-type p53 cell lines with mutant p53 cell lines that carry hotspot mutations in one of the following codons: 175, 248, and 273 and cell line with null p53 status.

An exemplary p53 human papilloma-virus cell line used is the Cervical Cancer HTB-3™ which contains approximately three integrated HPV16 copies per cell. ATCC confirmed this cell line as positive for the presence of Papilloma virus viral DNA sequences via PCR.

The p53 status of each line was previously sequenced and validated by the ATCC. The panels used are all useful for anti-cancer drug targeting or reactivation of mutant p53, as well as for studies related to p53 molecular mechanisms.

The cell line panels described above are treated by native cell derived vesicles (of animal origin) containing the p53 protein as described in the 'materials and experimental procedures section' above.

Dose Effect of Active Agent on Cell Growth Kinetics:

The dose dependent effect of cell derived vesicles on malignant cell growth kinetics was determined (FIG. 7, FIG. 13 and FIGS. 14A-C).

Effect of Concentrated Cell Derived Vesicles on Malignant Cell Lines Apoptosis:

Each cell line panel was divided into two test groups, i.e. treated and control.

Group 1: cells were maintained as per manufacturer's instruction and are not treated.

Group 2: cells were treated with the active agent prepared as described above and plated in 16-well plates for 24-72 hours. Seeding density is about 200,000 cells per 1 ml of media per well. Concentration of the active agent was determined based on the previous experiment (i.e. dose effect of active agent on cell growth kinetics).

After treatment, the cells were investigated for apoptosis using an apoptosis detection kit as described in the 'materials and experimental procedures section' above (FIGS. 6A-C).

Effect of Concentrated Cell Derived Vesicles on Cell Growth Kinetics:

Each cell line panel was divided into two test groups, i.e. treated and control.

Group 1: cells were maintained as per manufacturer's instruction and are not treated.

Group 2: cells were treated with the active agent prepared as described above and plate at 3000 cells per well in 96-well plates for 24-72 hours. Concentration of the active agent in medium was determined based on the previous experiment (i.e. dose effect of active agent on cell growth kinetics).

Cell morphology was observed under Nikon™ microscopy, and images of the indicated cell lines are captured by Olympus® digital camera (FIGS. 9A-B, FIGS. 10A-B and FIGS. 11A-B).

Cell growth kinetics is monitored for 10 days by CellTiter 96® AQueous One Solution Cell Proliferation Assay (Promega).

Example 3

In Vivo Studies: The Effect of Concentrated Cell Derived Vesicles on Cancer Progression in Mice Cells originating from the ATCC cell panels described in Table 1 above and demonstrating tumorigenic effect in nude mice are cultured in 75 ml tissue culture flasks as per manufacturer's instructions.

After the initial expansion phase, the cells are distributed into 24 well plates at a seeding density of about 200,000 cells per 1 ml of media per well. Cells are maintained as per manufacturer's instruction without any treatment or addition of active agent. Cells are harvested and inoculated intramuscularly into two groups (n=4 each) of nude mice. Following inoculation into nude mice, the tumorigenic cells produce palpable and measurable tumor masses at the site of injection. The tumor baring mice are treated using the active agent prepared as described in the 'materials and experimental procedures section' above, as follows:

Group 1:

1. Local/systemic application of any available MDM2 inhibitor.

2. Active agent is injected approximately 2 hours after MDM2 inhibitor injection. Injection is performed into the tumor area or systemically (depending on the cancer type).

Group 2: No further treatment (control group).

The nude mice are evaluated for tumor size at different time points after injection of the active ingredient.

Example 4

Anti-Cancer Effect of the Native Cell Derived Vesicles on Human Colorectal Adenocarcinoma Cells Malignant human colorectal adenocarcinoma cells containing a p53 mutation, HT-29, were used in these studies. These cells were cultured in the presence or absence of native microparticles obtained from rat cornea as described in detail in the 'materials and experimental procedures' section above (EXO_001, 50 μl per 1 ml of culture medium).

Based on visual inspection, after 3 days of culture, untreated HT-29 cells (Control) maintained their tumor phenotype and media discoloration was observed. In sharp contrast, in the presence of 50 μl native microparticles (EXO_001, as described in detail in the 'materials and experimental procedures' section above), the cell medium of the HT-29 treated cells was not discolored. Moreover, a significantly lower amount of HT-29 cells was evident in the treatment group (about 25-30% less) as compared to the control group (FIGS. 8A-B).

Example 5

The Effect of Native Cell Derived Vesicles on Malignant Cell Growth

HT-29 cells were seeded at a density of 200,000 cells in 1 ml of media per well in transwell-24. Twenty four hours after seeding, eight wells were treated with 100 μl of native microparticles (EXO_002) obtained from chicken cornea, as described in detail in the 'materials and experimental procedures' section above, while 100 μl of McCoy 5A medium was added to eight control wells. Cells were imaged 24, 48, and 72 hours after the beginning of treatment (FIGS. 9A-B, 10A-B and 11A-B). As illustrated from FIGS. 11A-B, 72 hours after the beginning of treatment, 61% cell growth inhibition was evident using Trypan Blue exclusion viability test (Table 2, below). The percentage of dead cells did not vary between treatment and control groups (less than 5% difference).

TABLE 2

Final cell number per well and average 72 hours after beginning of the treatment

| | Cell count | | | | |
|---|---|---|---|---|---|
| | Per well | | | | Average |
| Control (k cells/ml) | 1327 | 1360 | 1290 | 1338 | 1358.1 |
| | 1380 | 1320 | 1400 | 1450 | |
| Treated with 100 μl EXO_002 (k cells/ml) | 495 | 514 | 532 | 528 | 523.1 |
| | 570 | 515 | 496 | 535 | |
| Growth inhibition (%) | | | | | 61.5 |

Example 6

Stored Native Cell Derived Vesicles Maintain their Anti-Tumor Effect

Native microparticles (EXO_002) obtained from chicken cornea were stored frozen for about one year at -25° C. and thawed at 4° C. prior to use, as described in detail in the 'materials and experimental procedures' section above.

HT-29 cells were seeded at a density of 200,000 cells in 1 ml of media per well in transwell-24. One hour after seeding, eight wells were treated with 100 μl of native microparticles (EXO_002 as described in detail in the 'materials and experimental procedures' section above), while 100 μl of McCoy 5A medium was added to eight control wells. Cells were imaged after 24 hours. As illustrated in FIGS. 12A-B, freezing of the native microparticles did not affect their anti-tumor effect.

Example 7

Dose Effect of Native Cell Derived Vesicles on Malignant Cell Growth

HT-29 cells were seeded at a density of 200,000 cells in 1 ml of media per well in transwell-24. The wells were divided into three groups of eight wells. One hour later, two groups were treated with different doses of the native microparticles (EXO_002, as described in detail in the 'materials and experimental procedures' section above) (50 μl of EXO_002+50 μl of culture media, or 100 μl of EXO_002). The eight control wells were supplemented with 100 μl culture media. Images were taken 24 hours after beginning of treatment. As illustrated in FIGS. 13 and 14A-C the use of higher doses of native microparticles resulted in reduced cell proliferation.

Example 8

Native Cell Derived Vesicles' Effect on Malignant Cells Growth Kinetics

HT-29 cells were seeded at a density of 200,000 cells in 1 ml of media per well in transwell-24. In order to verify corneal origin specificity, the vitreous and iris tissue homogenate was used. The wells were divided into 4 groups of 6 wells. One hour later, two groups were treated with different doses of the native microparticles (EXO_002, as described in detail in the 'materials and experimental procedures' section above) (50 μl of EXO_002+50 μl of culture media or 100 μl of EXO_002) (FIG. 13). The remaining two groups of control cells were treated as follows: to the first control group of 6 wells 100 μl of culture media was added; to the second control group 100 μl of vitreous and iris tissue homogenate (prepared in the same way as EXO_002 agent) was added. Images were taken 24 hours after the treatment. As illustrated in FIGS. 15A-B and 16A-B, the effect is indeed specific to corneal epithelium and is completely abolished when adjacent tissues are used. These results are in accordance with the data previously provided [Tendler Y et al., (1999) supra; Pokroy R. et al., (2002) supra; Tendler Y et al. (2006) supra; Tendler Y et al. (2013) supra] that corneal epithelium comprises high levels of p53 while other eye tissues do not. Thus, only microparticles obtained from specific tissues are effective as anti-cancer agents likely due to their contents of p53 and absence of MDM2.

Example 9

The Effect of Native Cell Derived Vesicles on Apoptosis of Malignant Cells

HT-29 cells were seeded at a density of 200,000 cells in 1 ml of media per well in transwell-24. Twenty four hours after seeding, cells were treated with 100 μl of native microparticles (EXO_001, as described in detail in the 'materials and experimental procedures' section above). Twenty four hours later, apoptosis was determined using an Apoptotic Kit (Annexin V-FITC Kit) for detection of early-stage apoptosis (MEBCYTO) MBL, according to manufacturer instructions. As illustrated in FIGS. 6A-C, apoptosis is evident in treated cells (as indicated by green colored cells) whereas in the control group no apoptosis is evident (as indicated by the red colored cells).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of obtaining cell derived vesicles comprising an active wild-type p53, the method comprising:
   (i) treating non-human corneal epithelium cells with a DNA damaging agent, wherein said non-human corneal epithelium cells do not express recombinant p53; and
   (ii) isolating cell derived vesicles from said non-human corneal epithelium cells,
thereby obtaining said cell derived vesicles comprising said active p53.

2. The method of claim 1, wherein said active wild-type p53 comprises phosphorylated wild-type p53.

3. The method of claim 1, wherein said cell derived vesicles have a mean particle diameter of about 20 to about 200 nm.

4. The method of claim 1, wherein said cell derived vesicles comprise exosomes.

5. The method of claim 1, wherein an outer surface of said cell derived vesicles comprise a heterologous moiety for targeted delivery of said cell derived vesicles to a target cell.

6. The method of claim 1, wherein said cell derived vesicles are essentially devoid of intact cells.

7. The method of claim 1, wherein said cells are healthy cells.

8. The method of claim 1, wherein said cells are genetically non-modified cells.

9. The method of claim 1, wherein said cells are genetically modified cells.

10. The method of claim 1, wherein said cells have been treated with a MDM2 inhibitor.

11. The method of claim 1, wherein said DNA damaging agent is selected from the group consisting of a UV irradiation, a gamma irradiation, a chemotherapy, an oxidative stress, hypoxia, nutrient deprivation.

12. The method of claim 1, wherein said non-human cells are chicken cells.

* * * * *